(12) United States Patent
Takano et al.

(10) Patent No.: US 7,488,762 B2
(45) Date of Patent: Feb. 10, 2009

(54) TWO PASTE-TYPE GLASS IONOMER CEMENT

(75) Inventors: Satosi Takano, Kyoto (JP); Toshiyuki Nakatsuka, Kyoto (JP); Mikito Deguchi, Kyoto (JP); Shinji Urabe, Kyoto (JP); Toshimasa Ohnishi, Kyoto (JP)

(73) Assignees: Kabushiki Kaisha Shofu, Osaka (JP); Nagase Chemtex Corporation, Osaka (JP)

( * ) Notice: Subject to any disclaimer, the term of this patent is extended or adjusted under 35 U.S.C. 154(b) by 207 days.

(21) Appl. No.: 11/409,268

(22) Filed: Apr. 24, 2006

(65) Prior Publication Data

US 2006/0247330 A1 Nov. 2, 2006

(30) Foreign Application Priority Data

Apr. 25, 2005 (JP) ............................. 2005-126751

(51) Int. Cl.
*A61K 6/083* (2006.01)
(52) U.S. Cl. ..................... 523/117; 523/116; 433/228.1
(58) Field of Classification Search ................. 523/117, 523/116
See application file for complete search history.

(56) References Cited

U.S. PATENT DOCUMENTS

| | | | |
|---|---|---|---|
| 4,016,124 A | 4/1977 | Crisp et al. | |
| 4,342,677 A | 8/1982 | Muramatsu et al. | |
| 4,360,605 A | 11/1982 | Schmitt et al. | |
| 4,374,936 A | 2/1983 | Tomioka et al. | |
| 4,376,835 A | 3/1983 | Schmitt et al. | |
| 4,524,824 A | 6/1985 | Shimokobe et al. | |
| 4,591,384 A | 5/1986 | Akahane et al. | |
| 4,775,592 A | 10/1988 | Akahane et al. | |
| 4,806,381 A | 2/1989 | Engelbrecht | |
| 4,808,228 A | 2/1989 | Randklev | |
| 4,872,936 A | 10/1989 | Engelbrecht | |
| 4,900,697 A | 2/1990 | Akahane et al. | |
| 5,063,257 A | 11/1991 | Akahane et al. | |
| 5,130,347 A | 7/1992 | Mitra | |
| 5,290,172 A * | 3/1994 | Sakuma et al. .............. | 433/215 |
| 5,520,725 A | 5/1996 | Kato et al. | |
| 6,063,832 A | 5/2000 | Yuhda et al. | |
| 6,214,101 B1 | 4/2001 | Nakaseko | |
| 6,872,244 B2 | 3/2005 | Kobayashi et al. | |
| 7,090,721 B2 * | 8/2006 | Craig et al. ................... | 106/35 |

FOREIGN PATENT DOCUMENTS

| | | |
|---|---|---|
| EP | 0329268 | 8/1989 |
| EP | 0391619 | 10/1990 |
| GB | 1422337 | 1/1976 |
| GB | 1484454 | 9/1977 |
| GB | 1532954 | 11/1978 |
| GB | 2190372 | 11/1987 |
| JP | 5410010 | 5/1979 |
| JP | 5421858 | 8/1979 |
| JP | 558019 | 3/1980 |
| JP | 56-37964 | 9/1981 |
| JP | 57002209 | 1/1982 |
| JP | 57126406 | 8/1982 |
| JP | 595536 | 2/1984 |
| JP | 5923285 | 6/1984 |
| JP | 5938926 | 9/1984 |
| JP | 6034903 | 2/1985 |
| JP | 61215234 | 9/1986 |
| JP | 6150989 | 11/1986 |
| JP | 62149707 | 7/1987 |
| JP | 6310128 | 3/1988 |
| JP | 63182238 | 7/1988 |
| JP | 63201038 | 8/1988 |
| JP | 63225567 | 9/1988 |
| JP | 1308855 | 12/1989 |
| JP | 239465 | 9/1990 |
| JP | 02275731 | 11/1990 |
| JP | 262525 | 12/1990 |
| JP | 347107 | 2/1991 |
| JP | 359041 | 9/1991 |
| JP | 05097623 | 4/1993 |
| JP | 05331017 | 12/1993 |
| JP | 627047 | 4/1994 |
| JP | 670088 | 9/1994 |
| JP | 826925 | 1/1996 |
| JP | 8301717 | 11/1996 |
| JP | 2588702 | 12/1996 |

(Continued)

*Primary Examiner*—Tae H Yoon
(74) *Attorney, Agent, or Firm*—Novak, Druce & Quigg, LLP

(57) ABSTRACT

An object of the present invention is to provide a paste-type cement composition which while retaining adhesion to tooth substance, biocompatibility, surface curability and fluorine sustained-releasability which are the characteristics derived from the conventional glass ionomer cement, reduces water sensitivity which is shortcoming of the conventional glass ionomer cement, enables simple mixing operation, does not adversely affect on the various properties of a cured cement depending on a difference in operators or a skill degree, and can afford various stable properties. There is provided a two paste-type glass ionomer cement comprising a resin-based paste containing a hydrophobic polymerizable monomer and a polymer of acidic group-containing polymerizable monomers which are insoluble to each other, and a water-based paste containing a hydrophilic polymerizable monomer and water which are soluble to each other, in which an acid reactive filler is contained in at least one of pastes.

6 Claims, No Drawings

FOREIGN PATENT DOCUMENTS

| | | |
|---|---|---|
| JP | 2869078 | 12/1998 |
| JP | 11228327 | 8/1999 |
| JP | 2000026225 | 1/2000 |
| JP | 2000513339 | 10/2000 |
| JP | 3288698 | 3/2002 |
| JP | 2002087917 | 3/2002 |
| JP | 2003183112 | 7/2003 |
| JP | 3542683 | 4/2004 |
| WO | 9221314 | 12/1992 |
| WO | 9747272 | 12/1997 |

* cited by examiner

TWO PASTE-TYPE GLASS IONOMER CEMENT

TECHNICAL FIELD OF THE INVENTION

The present invention relates to a two paste-type glass ionomer dental cement which may be used in applications for cavity filling after caries treatment, cavity lining, root canal filling, cementation/adhesion of crown prosthetic materials such as metals, ceramics, composite resins and the like, cementation/adhesion of orthodontic brackets and bands and the like, core construction, pit and fissure sealing, temporary cementation/sealing, other applications relating to preventive dentistry. More particularly, the present invention relates to a two paste-type glass ionomer dental cement comprising a resin-based paste and a water-based paste, and this two paste-type glass ionomer dental cement is characterized in that the cement is cured via an acid-base reaction based on a specific combination of components and a polymerization reaction.

BACKGROUND ART

Conventionally, a dental cement has been used not only as cementation/adhesion in crown prosthetic materials represented by metal materials such as inlay, onlay, crown and the like but also in many dental applications such as filler, lining and base materials, cementation/adhesion for orthodontic brackets and bands and the like, temporary filling materials, temporary cementing materials, sealant, root canal filling materials, core construction materials and other preventive dentistry related materials.

In addition, regardless of many types of dental cement, all of the dental cement have advantages and disadvantages in operations and properties and, therefore, applications are determined depending on the advantages and disadvantages.

In the past, zinc phosphate cement which comprises mainly zinc oxide as a powder and an orthophosphoric acid aqueous solution as a liquid was mainly used as a cementing material in crown prosthetic materials such as molded metal materials. However, this kind of cement has disadvantages that a great pulp irritation occurs due to phosphoric acid at an earlier stage of setting, that properties vary depending on a mixing temperature because a setting reaction is an exothermic reaction, that prosthetic appliances are hold via mechanical interlock, and the like.

A carboxylate cement which comprises mainly zinc oxide as a powder and a poly(carboxylic acid) aqueous solution as a liquid sets by chelate of zinc ions released from the powder when the powder is eroded with the liquid and carboxyl groups which are side groups of the poly(carboxylic acid) comprised in the liquid. Since at the same time those carboxyl groups also chelate with metal elements such as calcium existing in tooth substance, this cement also has adhesiveness to tooth substance. This cement has an advantage that a pulp irritation is smaller and a disadvantage that a mechanical strength is lower comparing to the zinc phosphate cement.

A eugenol cement which comprises mainly zinc oxide as a powder and a eugenol oil as a liquid has an advantage as having analgesic, sedative and antiphlogistic effects to oral diseases, but its application is limited to temporary sealing or temporary cementation because its mechanical strength is low and has poor durability in oral cavities.

A resin cement comprising mainly an organic polymer or an inorganic filler as a powder and an acrylic polymerizable monomer as a liquid, and at least either of them contains a polymerization catalyst has adhesion to tooth substance and mechanical properties which are much more excellent than those of other cement.

However, it has a disadvantage that complicated pretreatments such as etching and primer applying to materials to be used are necessary, and that biocompatibility is poor, and the like.

In addition, since this cement cures via a polymerization reaction of polymerizable monomers, it is liable to undergo polymerization inhibition, and further it has a disadvantage that an unpolymerized layer of the polymerizable monomer exists on the surface of a cured resin cement. The existence of this unpolymerized layer causes discoloration or coloring in the cured resin cement, and generation of secondary caries in tooth substance around an unpolymerized layer to which bacteria adhered. In order to eliminate or reduce this unpolymerized layer, complicated handling such as covering the surface with an oxybarrier to block oxygen, irradiating with light and the like is required not only in pretreatment but also during and after a curing process.

A glass ionomer cement which comprises mainly an aluminosilicate glass containing elements such as fluorine, calcium, and the like as a powder and a poly(carboxylic acid) aqueous solution as a liquid exhibits a curing behavior similar to that of a carboxylate cement although types of the powder are different from each other.

The glass ionomer cement cures by chelate of calcium ions and aluminum ions released from the powder when the powder is eroded with the liquid and carboxyl groups which are side groups of the poly(carboxylic acid) comprised in the liquid.

Since those carboxyl groups also chelate with tooth substance, this cement also has adhesiveness to tooth substance. This cement shows a smaller pulp irritation and, thus, this glass ionomer cement is also excellent in biocompatibility.

Since the glass ionomer cement has excellent transparency which cannot be observed in other cements and a high mechanical strength, its application extends from merely use as adhesives to use as filling materials.

Further, the glass ionomer cement can persistently sustained-release a trace of fluorine from the set cement and has preventive effects such as suppression and prevention of secondary caries and reinforcement of tooth substance. Therefore, it is used as a preventive material.

For this glass ionomer cement, details are described in JP 54-21858A, JP 54-10010A, JP 61-50989A, JP 2-62525A and the like.

Although the glass ionomer cement has many advantages as described above, there is a disadvantage, so-called water sensitivity, that when a surface of the cement touches to water during setting, it dissolves in water and becomes cloudy. In order to reduce the water sensitivity as much as possible, it is required to set a cement immediately after applying it in an oral cavity, by shortening a time period (a setting time) when takes from applying in the oral cavity to setting.

Moreover, complicated procedure to mix a powder and a liquid are needed for the glass ionomer cement, and mixed status varies depending on operator's procedure carrying out the mixing procedure and their skill. Therefore, it is impossible to obtain stable properties. In order to obtain stable properties, it is required to sufficiently mix by lengthening a time period (a procedure time) from the onset of mixing to application in an oral cavity as long as possible.

However, since shortening a setting time and lengthening a procedure time conflict with each other and react on each other, it has been a great problem to obtain both an ideal long procedure time and an ideal short setting time. Accordingly, there are reported many technical attempts to invest a glass ionomer cement with a short setting time to set immediately after applying in an oral cavity before touching with water with maintaining a long procedure time to carry out a sufficient mixing.

For example, as attempts to glass compositions, disclosed are "an alkaline earth metal aluminofluorosilicate salt glass comprising strontium and a cement composition containing the same" in JP 63-182238A, "a glass composition comprising specific element components for use in a glass ionomer cement" in JP 61-215234A, "a glass powder comprising $ZrO_2$ and ZnO for a glass ionomer cement" in JP 2-275731A, "a lanthanum strontium fluoroaluminosilicate glass powder" in JP 5-331017A, "a fluoroaluminosilicate glass powder free of ions of alkali metals and specific alkaline earth metals" in JP 63-201038A, and the like.

As attempts to addition of the third components to a powder or a liquid, disclosed are "a dental cement composition comprising a water-insoluble tannic acid derivative" in JP 60-34903A and JP 63-10128A, "a dental cement setting solution of an acrylic acid-maleic acid copolymer comprising soluble organic carboxylic acid and a fluoro complex salt" in JP 59-46924A, "a dental cement setting solution of poly (acrylic acid) or copolymer of acrylic acid comprising an inorganic acid" in JP 56-37964A, "a dental cement setting solution of an acrylic acid-maleic acid copolymer comprising a fluoro complex salt and tartaric acid" in JP 59-38926A, "a dental cement setting solution comprising tetrahydrofuran-tetracarboxyl acid" in JP 59-24128A and JP 59-23285A, "a method for adding tartaric acid in a dental cement" in JP 55-8019A, and the like.

As attempts to treatment of a glass surface, disclosed are "a method for treating a surface of a glass powder with fluoride" in JP 3-59041A, "a method for delaying a setting reaction with poly(carboxylic acid) by washing a glass powder with acids to eliminate calcium and the like existing around the surface of the powder" in JP 59-5536A and JP 2-39465A, "a method for treating a surface of a glass powder by adding carboxylic acid in fine grinding glass lumps" in JP63-225567A, "a method for heat-treating a glass powder surface with carboxylic acid" in Japan Patent No. 2796461, and the like.

By these attempts, in any cases, some extent of improvements were observed with respect to water sensitivity, but prevention of water sensitivity has not been achieved. In addition, mixing procedure of a powder and a liquid is still complicated and, many problems remain that properties are influenced by differences in operators and their skills.

In addition, many reports are currently disclosed on cement compositions in which adhesion to tooth substance is improved by incorporating an acid-base reaction, which is a setting reaction of a glass ionomer cement without primer treatments required in use of a resin cement.

For example, disclosed are "a cement composition comprising a monomer having a polymerizable group and an ionic group at a side chain in the molecule" in JP 6-70088A and Japan Patent No. 2588702, JP 62-149707A and the like, "a dental cement composition free of water which essentially comprises a polymer of α-β unsaturated carboxylic acid and an inorganic component chelate with the polymer" in Japanese Patent No. 3542683 and JP 3-47107, and the like.

The above reports describe that due to incorporation of a monomer having a polymerizable group and an ionic group at a side chain in the molecule or a polymer of α-β unsaturated carboxylic acid into a cement composition, acidic groups in respective molecules cause an acid-base reaction with metal elements existing in the tooth substance such as calcium to improve adhesion to tooth substance.

However, in components constituting the cement, since water is not comprised as an essential component, an acid-base reaction does not occur in the inside of the cement composition and, accordingly, they differ from a glass ionomer cement in the structural aspect. Thus, properties other than adhesion to tooth substance which the glass ionomer cements have are not exerted.

These cement compositions are intended to incorporate water into the inside of the cement compositions by water absorption of the composition after curing to cause a secondary acid-base reaction and, a structural change also occurs accompanying the reaction. Therefore, material durability is concerned.

Recently, many reports are disclosed on a cement composition comprising a polymerizable monomer and a polymerization catalyst in addition to components constituting a glass ionomer cement (water, a polymer of α-β unsaturated carboxylic acid, fluoroaluminosilicate glass), and a cement composition comprising a monomer having an ionic group and a polymerizable group in its side chain instead of a polymer of α-β unsaturated carboxylic acid as a component constituting a glass ionomer cement, and further comprising a polymerizable monomer and a polymerizing catalyst.

For example, disclosed are "a cement composition comprising a monomer having an ionic group and a polymerizable group in its side chain" in Japan Patent No. 2869078 and JP 1-308855A, "a cement composition comprising a polymerizable monomer in addition to components constituting a glass ionomer cement" in JP 6-27047A, Japan Patent No. 3288698, JP 8-26925A, JP 8-301717A, JP 2000-26225A and JP 2002-87917A.

These kinds of cement compositions are called as a resin-modified glass ionomer cement and, as a curing mechanism, polymerization reactions of many types of monomers with chemical polymerization catalysts and photopolymerization catalysts are also adopted in addition to an essential reaction, an acid-base reaction, of a conventional glass ionomer cement. Consequently, even when water touches during curing, water sensitivity that a cured product becomes cloudy and brittle has been prevented and, their mechanical properties such as a bending strength and the like have been greatly improved. Further, some have not only adhesion to tooth substance such as an enamel, a dentin and the like but also adhesion to a metal, a porcelain, a composite resin and the like and, thus, they become significantly advanced materials.

However, since these cement compositions contain polymerizable monomers as a liquid component, they have disadvantages which are not observed in a glass ionomer cement, that polymerization is inhibited with oxygen during curing to generate an unpolymerized layer on a surface of a cured cement composition similar to that of a resin cement.

Similar to a conventional glass ionomer cement, a resin-modified glass ionomer cement cannot be prepared in a form of one package type based on the relationship between constituting components involving in an acid-base reaction, they should be prepared in a form of a divided package type, such as a powder-liquid type, a powder-paste type, a liquid-paste type, a paste-paste type and the like; and any glass ionomer cement is prepared mainly in a form of a powder-liquid type.

In a form of a powder-liquid type, a divisional mixing process, in which a powder is divided and mixed with a liquid stepwise upon its use, is generally carried out and mixing, which is a process repeating smear mixture thinly on a paper mixing plate to uniformly spread at a final stage of mixing, is also required in order to exert stable properties. These sequential processes are easy for skilled operators, but are difficult for operators with a little experience.

Further, in a resin-modified glass ionomer cement, since the viscosity of the liquid becomes high because the liquid contains a polymerizable monomer, miscibility of the powder and the liquid becomes worse to make mixing difficult. Moreover, a ratio between the powder and the liquid varies due to weighing variation when the powder is weighed on a measure and, therefore, intended properties or stable properties cannot be obtained.

Accordingly, reports are recently disclosed regarding the conventional glass ionomer cement or resin-modified glass ionomer cement in a two paste-type which is easy to mix regardless of operator's experience and skill by reducing complicated procedure such as weighing and divisional mixing as much as possible.

For example, disclosed is "the conventional glass ionomer cement composition in a two paste-type which comprises a polymer of α-β unsaturated carboxyl acid and water as a first paste, and a fluoroaluminosilicate glass powder, water and a water-soluble thickener as a second paste" in JP 2003-183112A. In this report, the second paste whose main component is water comprises a water-soluble thickener because a viscosity is invested to improve handling without using a polymerizable monomer. This cement composition is excellent in handling such as mixing because it is in a form of a two paste-type, but its mechanical strength deteriorates by influence of the water-soluble thickener. In addition, since the thickener is water-soluble, it inhibits the acid-base reaction to delay a setting time and, thereby, a disadvantage of the conventional glass ionomer cement, water sensitivity, tends to become worse.

JP 11-228327A discloses "a cement composition comprising a polymer of α-β unsaturated carboxylic acid, water and a filler material which does not react with the polymer of α-β unsaturated carboxylic acid as a first paste and a fluoroaluminosilicate glass and a polymerizable monomer free of an acidic group as a second paste". In this cement composition, it is essential that constituting components causing an acid-base reaction, water and a polymer of α-β unsaturated carboxylic acid, are contained only in the first paste and a fluoroaluminosilicate glass is contained only in the second paste. In addition, in the first paste, the polymer of α-β unsaturated carboxylic acid coexists in a state where it and water are soluble to each other.

JP 2000-513339A discloses "a multiple liquid type ionomer cement comprising an organic composition which contains a polymerizable hydrophilic component and an acid functional compound (a polymer) and is substantially free of water, wherein they are soluble to each other, and an aqueous composition, which contains water and an aqueous component which is soluble to water and also disclosed is that an acid reactive filler may be comprised in any of compositions".

In this multiple liquid type ionomer cement, it is essential that the acid functional compound (a polymer) which is an acid-base reactive constituting components is contained only in the organic composition and water is contained only in the aqueous composition, respectively, and the acid reactive filler is contained at least one of the compositions. Further, in the organic composition, the acid functional compound (a polymer) coexists in a state where it and the hydrophilic component are soluble to each other.

However, according to constitutions of the components comprised in the cement compositions disclosed in JP 11-228327A and JP 2000-513339A, since the acid-base reaction and the polymerization reaction do not occur with good balance, it is difficult to manifest characteristic properties from a glass ionomer cement, adhesion to tooth substance, surface curability, biocompatibility and fluorine sustained-releasabilty resulting in materials having properties similar to those of resin cement. In addition, in any of the cement compositions, a polymer of α-β unsaturated carboxylic acid or an acid functional compound (a polymer) involving in the acid-base reaction respectively is comprised in a soluble state. When the cement composition is cured in this state, polymerization is inhibited with oxygen during curing similar to a resin cement to form an unpolymerized layer on a surface of the cured cement. This unpolymerized layer may cause discoloration or coloration, alternatively bacteria may attach to this unpolymerized layer to cause secondary caries in the tooth substance around the area thereof.

[Patent Document 1] JP 54-21858A
[Patent Document 2] JP 54-10010A
[Patent Document 3] JP 61-50989A
[Patent Document 4] JP 2-62625A
[Patent Document 5] JP 63-182238A
[Patent Document 6] JP 61-215234A
[Patent Document 7] JP 2-275731A
[Patent Document 8] JP 5-331017A
[Patent Document 9] JP 63-201038A
[Patent Document 10] JP 60-34903A
[Patent Document 11] JP 63-10128A
[Patent Document 12] JP 59-46924A
[Patent Document 13] JP 56-37964A
[Patent Document 14] JP 59-38926A
[Patent Document 15] JP 59-24128A
[Patent Document 16] JP 59-23285A
[Patent Document 17] JP 55-8019A
[Patent Document 18] JP 3-59041A
[Patent Document 19] JP 59-5536A
[Patent Document 20] JP 2-39465A
[Patent Document 21] JP 63-225567A
[Patent Document 22] Japan Patent No. 2796461
[Patent Document 23] JP 6-70088A
[Patent Document 24] Japan Patent No. 2588702
[Patent Document 25] JP 62-149707A
[Patent Document 26] Japan Patent No. 3542683
[Patent Document 27] JP 3-47107A
[Patent Document 28] Japan Patent No. 2869078
[Patent Document 29] JP 1-308855A
[Patent Document 30] JP 6-27047A
[Patent Document 31] Japan Patent No. 3288698
[Patent Document 32] JP 8-26925A
[Patent Document 33] JP 8-301717A
[Patent Document 34] JP 2000-26225A
[Patent Document 35] JP 2002-87917A
[Patent Document 36] JP 2003-183112A.
[Patent Document 37] JP 11-228327A
[Patent Document 38] JP 2000-513339A

DISCLOSURE OF THE INVENTION

[Problem to be Solved by the Invention]

In view of the above situation, a paste type cement composition has been demanded, which has characteristics derived from a conventional glass ionomer cement: adhesion to tooth substance, biocompatibility, surface curability and fluorine sustained-releasability, and reduces an disadvantage of the conventional glass ionomer cement: water sensitivity, in which stable properties can be obtained because mixing can be easily carried out and those properties are not influenced by differences in operators and their skills.

Thus, the problems of the present invention is to provide a dental glass ionomer cement having the above-mentioned characteristics.

[Means for Solving the Problem]

The present inventors have made every effort to solve the above problems, in resulting they have invented a dental glass ionomer cement composition which comprises two pastes consisting of a resin-based paste comprising an organic component as an essential component, and a water-based paste comprising an aqueous component as an essential component.

More particularly, the present invention provides a two paste-type glass ionomer cement which comprises a resin-based paste and a water-based paste, which is characterized in that:

the resin-based paste comprises (a) a hydrophobic polymerizable monomer and (b) a polymer of acidic group-containing polymerizable monomers, wherein (a) the hydrophobic polymerizable monomer and (b) the polymer of acidic group-containing polymerizable monomers are insoluble to each other, and the water-based paste comprises (c) a hydrophilic polymerizable monomer and (d) water, wherein (c) the hydrophilic polymerizable monomer and (d) the water are soluble to each other, and wherein (1) at least one of the resin-based paste and the water-based paste contains (e) an acid reactive filler and (f) a polymerization catalyst together;

(2) the resin-based paste contains (e) an acid reactive filler and the water-based paste contains (f) a polymerization catalyst; or (3) the resin-based paste contains (f) a polymerization catalyst and the water-based paste contains (e) an acid reactive filler.

The two paste-type glass ionomer cement according to the present invention is characterized in that a total amount of (e) the acid reactive filler, (b) the polymer of acidic group-containing polymerizable monomers and (d) the water is in a range of 40 to 90 parts by weight per 100 parts by weight of the glass ionomer cement, and (e) the acid reactive filler: (b) the polymer of acidic group-containing polymerizable monomers: (d) the water is in a range of 1:0.1-2.9:0.1-3.6.

When a total amount of the acid reactive filler, the polymer of acidic group-containing polymerizable monomers and water is in the above range, an acid-base reaction based on these three components and a polymerization reaction based on a variety of polymerizable monomers occur with a good balance in a curing reaction.

Thereby, unlike the conventional resin-modified glass ionomer cement, the present invention allows to maintain the characteristics derived from the conventional glass ionomer cement, biocompatibility, adhesion to tooth substance and surface curability, to improve the disadvantage of the glass ionomer cement, mechanical strength, and to control water sensitivity.

The two paste-type glass ionomer cement according to the present invention is characterized in that the resin-based paste comprises (g) an acidic group-containing polymerizable monomer.

Thereby, the acid-base reaction between the polymer of acidic group-containing polymerizable monomers and the acid reactive filler in the presence of water is enhanced and adhesion to tooth substance (enamel and dentin) is increased and, further, adhesion to metals, resins and composite resins may be invested.

The two paste-type glass ionomer cement according to the present invention is characterized in that (b) the polymer of acidic group-containing polymerizable monomers is a polymer of an α-β unsaturated carboxylic acidic group-containing polymerizable monomer.

Thereby, the acid-base reaction with the acid reactive filler in the presence of water occurs effectively and the characteristics of the conventional glass ionomer cement, biocompatibility, adhesion to tooth substance and surface curability may be achieved at a high level.

The two paste-type glass ionomer cement according to the present invention is characterized in that (e) the acid reactive filler is a fluorine-containing radiopaque acid reactive glass filler which comprises fluorine and an element having radiopacity.

Thereby, fluorine sustained-releasability, color tone compatibility and radiopacity may be invested in addition to the above characteristics of the conventional glass ionomer cement.

The two paste-type glass ionomer cement according to the present invention is characterized in that (f) the polymerizing catalyst is a barbituric acid derivative or an organic peroxide-tertiary amine redox catalyst or a combination thereof.

Thereby, a polymerization reaction of the resin components in the presence of water occurs together with the acid-base reaction based on the three components of the acid reactive filler, water and the polymer of acidic group-containing polymerizable monomers, the disadvantages of the conventional glass ionomer cement, low mechanical strength and water sensitivity may be improved.

[Effects of the Invention]

According to the present invention, a dental glass ionomer cement can be provided, which has excellent biocompatibility, fluorine sustained-releasability and surface curability, all of which the conventional glass ionomer cement has, and reduces the disadvantage of the conventional glass ionomer, water sensitivity, and also has a high level mechanical strength.

In addition, the dental glass ionomer cement according to the present invention is in a form of a two paste-type and powder and liquid have been previously prepared as pastes, allowing at-once mixing, without requiring divisional mixing.

Further, since the dental glass ionomer cement according to the present invention exhibits neither sticking, dropping nor stringiness and is in a cream-like form with easy handling, it has an excellent handling property in which any operator from beginners to skilled people can exert stable and non-deviate properties.

BEST MODE FOR CARRYING OUT THE INVENTION

The two paste-type dental glass ionomer cement according to the present invention (hereinafter referred to as "the present cement composition") is a glass ionomer cement comprising a resin-based paste and a water-based paste.

In the present cement composition, the resin-based paste comprises (a) a hydrophobic polymerizable monomer and (b) a polymer of acidic group-containing polymerizable monomers, wherein (a) the hydrophobic polymerizable monomer and (b) the polymer of acidic group-containing polymerizable monomers are insoluble to each other.

In the resin-based paste, since (a) the hydrophobic polymerizable monomer and (b) the polymer of acidic group-containing polymerizable monomers are insoluble to each other, (b) the polymer of acidic group-containing polymerizable monomers exists in a particulate state, and upon controlling of this particle size, a mixing property between the resin-based paste and the water-based paste may be improved. In the water-based paste, since (c) the hydrophilic polymerizable monomer and (d) the water are soluble to each other, when mixed with the resin-based paste, they can be uniformly mixed so as to dissolve the polymer of acidic group-containing polymerizable monomers in the resin-based paste to cause an acid-base reaction, exhibiting properties which are intended in the present invention.

Further, since the present cement composition is required to comprise (e) an acid reactive filler and (f) a polymerization catalyst, it is characterized in that (1) at least one of the resin-based paste and the water-based paste contains (e) an acid reactive filler and (f) a polymerization catalysis together; (2) the resin-based paste contains (e) an acid reactive filler and the water-based paste contains (f) a polymerization catalyst; or (3) the resin-based paste contains (f) a polymerization catalyst and the water-based paste contains (e) an acid reactive filler.

The present cement composition cures via an acid-base reaction based on the three components of (e) the acid reactive filler, (b) the polymer of acidic group-containing polymerizable monomers and (d) water as well as a polymerization reaction based on the three components of various organic compounds having, polymerizable groups of (a) the hydrophobic polymerizable monomer and (c) the hydrophilic polymerizable monomer and (f) the polymerization catalyst occurred by mixing the resin-based paste and the water-based paste comprised of the cement composition.

Among these curing reactions, the acid-base reaction involves not only in curing of the present cement composition but also in adhesiveness of the present cement composition to tooth substance, for example, the acid-base reaction occurs with metal elements such as calcium existing in tooth substance similarly.

Important requirements for exhibiting excellent properties by the present cement composition are a constitution of components comprised in each of the resin-based paste and the water-based paste comprised in the cement composition, a mixture state of the organic components contained in the resin-based paste, and a mixture state of the aqueous components contained in the water-based paste.

The percentages or ratios of constituting components contained in the present cement composition, which involve in the acid-base reaction, are also important requirements.

A component contained in the resin-based paste constituting the present cement composition, (a) the hydrophobic polymerizable monomer is an essential component for generating a polymerization reaction in the presence of a polymerization catalyst when the resin-based paste and the water-based paste are mixed, and it may be used without any limitation regardless of types of radically polymerizable unsaturated groups and in either of monofunctional and multifunctional, as far as it is a polymerizable monomer showing hydrophobicity.

The "hydrophobic polymerizable monomer" referred herein is defined as a polymerizable monomer whose solubility is less than 10 parts by weight per 100 parts by weight of water at 23° C. Specifically, a polymerizable monomer 10 g is added to 100 g of water at 23° C. in a sample bottle, and they are mixed for 10 minutes. After 10 minutes for standing, the mixture is observed in the bottle. When phase separation is observed in the mixture, the polymerizable monomer is considered as a hydrophobic polymerizable monomer.

Examples of the radically polymerizable unsaturated groups which hydrophobic polymerizable monomer have, include a (meth)acryloyl group, a styryl group, a vinyl group, and an aryl group and, in particular, it is preferable to use a hydrophobic polymerizable monomer having a (meth)acryloyl group as an unsaturated group.

In addition, these hydrophobic polymerizable monomers may contain together, as far as hydrophobic, other functional group including an acidic group such as a carboxylic group, a phosphoryl group, a phosphonyl group and the like; an alkyl group; halogen; an amino group; a glycidyl group and; a hydroxide group.

Among the hydrophobic polymerizable monomers, hydrophobic polymerizable monomers in which the radical polymerizable unsaturated group is a (math)acryloyl group are specifically listed below.

Examples of the hydrophobic polymerizable monomer containing a monofunctional group include (meth)acrylic acid esters such as methyl(meth)acrylate, ethyl (meth)acrylate, butyl(meth)acrylate, hexyl(meth)acrylate, tetrahydrofurfuryl(meth)acrylate, glycidyl(meth)acrylate, lauryl(meth)acrylate, cyclohexyl(meth)acrylate, benzyl (meth)acrylate, aryl(meth)acrylate, 2-ethoxyethyl (meth)acrylate, methoxy polyethylene glycol (meth)acrylate, and isobonyl(meth)acrylate; silane compounds such as γ-(meth)acryloyloxypropyltrimethoxysilane, and γ-(meth)acryloyloxypropyltriethoxysilane; nitrogen-containing compounds such as 2-(N,N-dimethylamino)ethyl(meth)acrylate.

Examples of an aromatic hydrophobic polymerizable monomer containing two functional groups include, 2,2-bis (4-(meth)acryloyloxyphenyl)propane, 2,2-bis(4-(3-(meth) acryloyloxy-2-hydroxypropoxy)phenyl)propane, 2,2-bis(4-(meth)acryloyloxyethoxyphenyl)propane, 2,2-bis(4-(meth) acryloyloxydiethoxyphenyl)propane, 2,2-bis(4-(meth) acryloyloxytetraethoxyphenyl)propane, 2,2-bis(4-(meth) acryloyloxypentaethoxyphenyl)propane, 2,2-bis(4-(meth) acryloyloxydipropoxyphenyl)propane, 2-(4-(meth) acryloyloxyethoxyphenyl)-2-(4-(meth) acryloyloxydiethoxyphenyl)propane, 2-(4-(meth) acryloyloxydiethoxyphenyl)-2-(4-(meth) acryloyloxytriethoxyphenyl)propane, 2-(4-(meth) acryloyloxydipropoxyphenyl)-2-(4-(meth) acryloyloxytriethoxyphenyl)propane, 2,2-bis(4-(meth) acryloyloxydipropoxyphenyl)propane, and 2,2-bis(4-(meth) acryloyloxyisopropoxyphenyl)propane.

Examples of an aliphatic hydrophobic polymerizable monomer containing two functional groups include, ethylene glycol di(meth)acrylate, diethylene glycol di(meth)acrylate, triethylene glycol di(meth)acrylate, butylene glycol di(meth) acrylate, neopentyl glycol di(meth)acrylate, propylene glycol di(meth)acrylate, 1,3-butanediol di(meth)acrylate, 1,4-butanediol di(meth)acrylate, 1,6-hexanediol di(meth)acrylate, and di-2-(meth)acryloyloxyethyl-2,2,4-trimethylhexamethylenedicarbamate.

Examples of an aliphatic hydrophobic polymerizable monomer containing three functional groups include, trimethylolpropane tri(meth)acrylate, trimethylolethane tri (meth)acrylate, and trimethylol propane tri(meth)acrylate.

Examples of an aliphatic hydrophobic polymerizable monomer containing four functional groups include, pentaerythritol tetra(meth)acrylate, and pentaerythritol tetraacrylate.

Examples of a urethane hydrophobic polymerizable monomer include, di(meth)acrylate having two or three or more of functional groups, which is derived from adducts between a polymerizable monomer having a hydroxy group such as 2-hydroxyethyl(meth)acrylate, 2-hydroxypropyl (meth) acrylate and 3-chloro-2-hydroxypropyl(meth)acrylate and a diisocyanate compound such as methylcyclohexane diisocyanate, methylene bis(4-cyclohexylisocyanate), hexamethylene diisocyanate, trimethylhexamethylene diisocyanate, isophorone diisocyanate, diisocyanatomethylbenzene and 4,4-diphenylmethane diisocyanate.

In addition, not only monomers having a short main chain but also oligomers, prepolymers, polymers having a long main chain may be used without any limitation, as far as they are compounds having a (meth)acrylate group.

The above hydrophobic polymerizable monomers are not limited to the above listed ones, and they may be used alone or in a combination of plural.

Among these hydrophobic polymerizable monomers, those having solubility less than 5 parts by weight per 100 parts by weight of water at 23° C. are preferable, and those having solubility less than 1 parts by weight per 100 parts by weight of water at 23° C. are more preferable. Specifically, it is preferable to use 2,2-bis(4-(3-methacryloyloxy-2-hydroxypropoxy)phenyl)propane (Bis-GMA), 2,2-bis(4-methacryloyloxyethoxyphenyl)propane (D-2.6E), di(methacryloyloxyethyl)-2,2,4-trimethylhexamethylene diurethane (UDMA), triethylene glycol dimethacrylate (TEGDMA), neopentyl glycol di(meth)acrylate, and trimethylolpropane trimethacrylate.

A component contained in the resin-based paste constituting the present cement composition, (b) the polymer of acidic group-containing polymerizable monomers is an essential component for generating a acid-base reaction in the presence of water when the resin-based paste and the water-based paste are mixed, and it may be used without any limitation, as far as it is a polymer obtainable by polymerizing alone a polymerizable monomer having at least one or more of acidic groups in the molecule or by copolymerizing two or more of them.

In addition, as (b) the polymer of acidic group-containing polymerizable monomers, those obtainable by copolymerizing a polymerizable monomer having at least one or more of acidic groups in the molecule and a polymerizable monomer without an acidic group may also be used.

There is no problem where the resin-based paste contains these polymers of acidic group-containing polymerizable monomers alone or in a combination of plural.

Kinds of the acidic group which the acidic group-containing polymerizable monomer capable of being used for obtaining the polymer of acidic group-containing polymerizable monomers, is not particularly limited, and polymerizable monomer having any type of an acidic group may be used. In addition, they may be used without any limitation regardless of the number or type of radical polymerizable unsaturated groups (monofunctional groups or multifunctional groups) of the acidic group-containing polymerizable monomer.

Specifically, examples of the acidic groups of the acidic group-containing polymerizable monomer are not limited to, but include a phosphoryl group, a pyrophosphoryl group, a phosphonyl group, a carboxyl group, a sulfonyl group, and a thiophosphoryl group.

Specifically, examples of the unsaturated groups of the acidic group-containing polymerizable monomer are not limited to, but include a (meth)acryloyl group, a styryl group, a vinyl group, and an aryl group. It is preferable that the acidic group-containing polymerizable monomer has a (meth)acryloyl group among these unsaturated groups.

Further, these polymerizable monomers having an acidic group may contain together other functional groups such as an alkyl group, halogen, an amino group, a glycidyl group, and a hydroxy group.

Polymerizable monomers having an acidic group which have a (meth)acryloyl group as an unsaturated group and which may be used for obtaining polymers of acidic group-containing polymerizable monomers are specifically listed below.

Examples of an acidic group-containing polymerizable monomer which has a phosphoryl group are not limited to, but include polymerizable monomers having an acidic group such as (meth)acryloyloxymethyl dihydrogen phosphate, 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyeicosyl dihydrogen phosphate, di(meth)acryloyloxyethyl hydrogen phosphate, di(meth)acryloyloxybutyl hydrogen phosphate, di(meth)acryloyloxyhexyl hydrogen phosphate, di(meth)acryloyloxyoctyl hydrogen phosphate, di(meth)acryloyloxynonyl hydrogen phosphate, di(meth)acryloyloxydecyl hydrogen phosphate, 1,3-di(meth)acryloyloxypropyl-2-dihydrogenphosphate, 2-(meth)acryloyloxyethylphenyl hydrogen phosphate, 2-(meth)acryloyloxyethyl 2'-bromoethyl hydrogen phosphate, and (meth)acryloyloxyethyl phenyl phosphonate.

Examples of an acidic group-containing polymerizable monomer which has a pyrophosphoryl group are not limited to, but include, polymerizable monomers having an acidic group such as di[2-(meth)acryloyloxyethyl]pyrophosphate, di[3-(meth)acryloyloxypropyl]pyrophosphate, di[4-(meth)acryloyloxybutyl]pyrophosphate, di[5-(meth)acryloyloxypentyl]pyrophosphate, di[6-(meth)acryloyloxyhexyl]pyrophosphate, di[7-(meth)acryloyloxyheptyl]pyrophosphate, di[8-(meth)acryloyloxyoctyl]pyrophosphate, di[9-(meth)acryloyloxynonyl]pyrophosphate, di[10-(meth)acryloyloxydecyl]pyrophosphate, di[12-(meth)acryloyloxydodecyl]pyrophosphate, tetra[2-(meth)acryloyloxyethyl]pyrophosphate, and tri[2-(meth)acryloyloxyethyl]pyrophosphate.

Examples of an acidic group-containing polymerizable monomer which has a phosphonyl group are not limited to, but include polymerizable monomers having an acidic group such as 5-(meth)acryloyloxypentyl-3-phosphonopropionate, 6-(meth)acryloyloxyhexyl-3-phosphonopropionate, 10-(meth)acryloyloxydecyl-3-phosphonopropionate, 6-(meth)acryloyloxyhexyl-3-phosphonoacetate, and 10-(meth)acryloyloxydecyl-3-phosphonoacetate.

Examples of an acidic group-containing polymerizable monomer which has a carboxyl group are not limited to, but include polymerizable monomers having an acidic group such as (meth)acrylic acid, 2-chloro(meth)acrylic acid, 3-chloro(meth)acrylic acid, 2-cyano(meth)acrylic acid, aconitic acid, mesaconic acid, maleic acid, maleic anhydride, itaconic acid, itaconic anhydride, fumaric acid, glutaconic acid, citraconic acid, utraconic acid, 1,4-di(meth)acryloyloxyethylpyromellitic acid, 6-(meth)acryloyloxynaphthalene-1,2,6-tricarboxylic acid, 1-buten 1,2,4-tricarboxylic acid, 3-buten 1,2,3-tricarboxylic acid, N-(meth)acryloyl-p-aminobenzoic acid, N-(meth)acryloyl-5-aminosalicylic acid, 4-(meth)acryloyloxyethyltrimellitic acid and anhydride thereof, 4-(meth)acryloyloxybutyltrimellitic acid and anhydride thereof, 2-(meth)acryloyloxybenzoic acid, β-(meth)acryloyloxyethyl hydrogen succinate, (meth)acryloyloxyethyl hydrogen maleate, 11-(meth)acryloyloxy-1,1-undecanedicarboxylic acid, p-vinylbenzoic acid, 4-(meth)acryloyloxyethoxycarbonylphthalic acid, 4-(meth)acryloyloxybutyloxycarbonylphthalic acid, 4-(meth)acryloyloxyhexyloxycarbonylphthalic acid, 4-(meth)acryloyloxyoctyloxycarbonylphthalic acid, 4-(meth)acryloyloxydecyloxycarbonylphthalic acid and anhydride thereof, 5-(meth)acryloylaminopentylcarboxylic acid, 6-(meth)acryloyloxy-1,1-hexanedicarboxylic acid, 8-(meth)acryloyloxy-1,1-octanedicarboxylic acid, 10-(meth)acryloyloxy-1,1-decanedicarboxylic acid, and 11-(meth)acryloyloxy-1,1-undecanedicarboxylic acid.

Examples of an acidic group-containing polymerizable monomer which has a sulfonyl group are not limited to, but include polymerizable monomers having an acidic group such as 2-(meth)acrylamido-2-methylpropanesulfonic acid, styrenesulfonic acid, 2-sulfoethyl(meth)acrylate, 4-(meth)acryloyloxybenzenesulfonic acid, and 3-(meth)acryloyloxypropanesulfonic acid.

Examples of an acidic group-containing polymerizable monomer which has a thiophosphoryl group are not limited to, but include polymerizable monomers having an acidic group such as 10-(meth)acryloyloxydecyldihydrogendithiophosphate.

Although polymerized monomers having an acidic group which may be used for obtaining a polymer of a polymerized monomer having an acidic group are listed, they are not limited to those listed monomers and a derivative of an acidic group-containing polymerizable monomer such as partially neutralized metal salts, ammonium salts and acid chloride and the like may also be used to an extent that they do not affect the acid-base reaction.

It is preferable to use a polymer of acidic group-containing polymerizable monomers obtainable by polymerizing alone each of α-β unsaturated carboxylic acidic group-containing polymerizable monomers having an acidic group among those acidic group-containing polymerizable monomers having an acidic group or by copolymerizing two or more of them.

The α-β unsaturated carboxylic acidic group-containing polymerizable monomers are not particularly limited and they may be used regardless of the number of carboxylic groups in the molecule or the existence of a carboxylic anhydride group or other substituents.

Specifically, examples of an α-β unsaturated carboxylic acidic group-containing polymerizable monomers are not limited to, but include (meth)acrylic acid, 2-chloro(meth)acrylic acid, 3-chloro(meth)acrylic acid, 2-cyano(meth)acrylic acid, aconitic acid, mesaconic acid, maleic acid, maleic anhydride, itaconic acid, itaconic anhydride, fumaric acid, glutaconic acid, citraconic acid, utraconic acid, 1-buten 1,2,4-tricarboxylic acid; and 3-buten 1,2,3-tricarboxylic acid.

It is more preferable to use, among them, homopolymers of acrylic acid; or copolymers of acrylic acid and maleic acid, acrylic acid and maleic anhydride, acrylic acid and itaconic acid, acrylic acid and 3-buten 1,2,3-tricarboxylic acid, as a polymer of acidic group-containing polymerizable monomers in the resin-based paste constituting the present cement composition.

It is preferable that a weight average molecular weight of these polymers of the polymerizable monomers having an acidic group is in a rage of 1000 to 80000, more preferable in a rage of 5000 to 40000.

When a weight average molecular weight of the polymers of acidic group-containing polymerizable monomers decreases below 1000, a mechanical strength of a cured cement composition tends to decrease too much, and adhesion to tooth substance decreases to cause problems in durability of the cement composition. Moreover, due to the existence of lower molecular weight polymers, odor and pungency are concerned.

On the other hand, when a weight average molecular weight of the polymers of acidic group-containing polymerizable monomers increases above 80000, viscosity of mixture of the resin-based paste and the water-based paste constituting the cement composition becomes hard when mixing to deteriorate a mixing property.

Since the organic components contained in the resin-based paste constituting the present invention: (a) the hydrophobic polymerizable monomer and (b) the polymer of acidic group-containing polymerizable monomers are insoluble to each other, (b) the polymer of acidic group-containing polymerizable monomers exists in a solid state, that is, as particles in the resin-based paste. Therefore, a particle size of the polymer of acidic group-containing polymerizable monomers affects the mixing property for mixing the resin-based paste and the water-based paste constituting the present cement composition. The mixing property is considered to be affected by a dissolving speed of the polymer of acidic group-containing polymerizable monomers into water contained in the water-based paste during mixing the resin-based paste and the water-based paste.

Thus, a particle size of the polymer of a polymerizing monomer having an acidic group is preferably that passing through an 80 mesh sieve and not passing a 350 mesh sieve, more preferably that passing through a 125 mesh sieve and not passing a 250 mesh sieve when sifting with a JIS standard sieve. When a polymer of acidic group-containing polymerizable monomers whose particle size is that passing through a 350 mesh sieve is used, a feeling in mixing becomes heavier because the polymer easily dissolves into water contained in the water-based paste during mixing. On the other hand, when a polymer of acidic group-containing polymerizable monomers whose particle size is that not passing through an 80 mesh sieve is used, a felling in mixing is light, but a mixing property is affected, for example, the mixture becomes rough because the particle size is too large.

Important requirements for exhibiting excellent properties by the present cement composition are a constitution and an amount of components comprised in each of the resin-based paste and a mixture state of the organic components contained in the resin-based paste.

The resin-based paste constituting the present cement composition is substantially free of water and may comprise organic components: (a) a hydrophobic polymerizable monomer and (b) a polymer of a polymerizable monomer having an acidic group as essential components, and may further comprise inorganic components: (e) an acid reactive filler and (f) a polymerization catalyst.

That among these components, the organic components: (a) the hydrophobic polymerizable monomer and (b) the polymer of a polymerization monomer having an acidic group are insoluble to each other is an important requirement for decreasing formation of a resin-rich layer, an unpolymerized layer, on a surface of a cement composition after curing.

Amounts of respective components constituting the organic components contained in the resin-based paste are preferably in a range of 20 to 70 parts by weight, more preferably in a rage of 40 to 60 parts by weight for (b) the polymer of acidic group-containing polymerizable monomers per 100 parts by weight of the organic components which is a sum of: (a) the hydrophobic polymerizable monomer and (b) the polymer of acidic group-containing polymerizable monomers.

When an amount of the polymer of acidic group-containing polymerizable monomers decreases below 20 parts by weight, it is difficult for an acid-base reaction to occur according to the balance with an amount of the acid reactive filler, and characteristics of a glass ionomer cement such as adhesion to tooth substance tend to deteriorate. On the other hand, when an amount of the polymer of acidic group-containing polymerizable monomers increases over 70 parts by weight, the cured cement composition tends to absorb water so that it is possible to cause reduction in mechanical properties, increase in solubility and the like because a large amount of polymer of acidic group-containing polymerizable monomers having unreacted acidic groups which are not involved in the acid-base reaction according to the balance with an amount of the acid reactive filler remains in the cement composition. In addition, since the polymer of acidic group-containing polymerizable monomers is a solid, it is possible that a paste cannot be formed.

By containing of (g) an acidic group-containing polymerizable monomer in the resin-based paste constituting the present cement composition, adherability to metals, resins, composite resins and tooth substance (enamel and dentin) can be invested, and the adherability can be enhanced.

The acidic group-containing polymerizable monomer has adherability to materials such as metals, resins, composite resins and tooth substance (enamel and dentin), and also involves in a curing reaction, for example, it generates an acid-base reaction with an acid reactive filler in the presence of water because it has an acidic group similar to the polymer of acidic group-containing polymerizable monomers.

In addition, (g) an acidic group-containing polymerizable monomer itself is not particularly limited regardless of whether it is soluble or insoluble to (a) a hydrophobic polymerizable monomer, as far as (a) the hydrophobic polymerizable monomer and (b) the polymer of an acid group-containing polymerizable monomer are soluble to each other when an acidic group-containing polymerizable monomer is added to the resin-based paste.

An acidic group-containing polymerizable monomer contained in the resin-based paste constituting the present cement composition may be used regardless of types of acidic groups or unsaturated groups and the like, as far as polymerizable monomer having at least one acidic group in the molecule.

Specifically, an acidic group-containing polymerizable monomer includes, for example, the same acidic group-containing polymerizable monomer as those may be used in obtaining a polymer of acidic group-containing polymerizable monomers. The acidic group-containing polymerizable monomer is not particularly limited and may be the same as or different from those may be used in obtaining a polymer of acidic group-containing polymerizable monomers.

In addition, these acidic group-containing polymerizable monomers may be used alone or in a combination of plural of them. Further, a derivative of an acidic group-containing polymerizable monomer such as partially neutralized metal salts, ammonium salts and acid chloride may also be used to an extent that they do not affect the acid-base reaction.

It is preferable to use 10-methacryloyloxydecyldihydrogenphosphate, 6-methacryloyloxyhexyl-3-phosphonoacetate, 4-methacryloyloxyethyltrimellitic acid and anhydride thereof, and 4-acryloyloxyethyltrimellitic acid and anhydride thereof among these acidic group-containing polymerizable monomers.

A content of (a) the acidic group-containing polymerizable monomer contained in a resin-based paste constituting the cement composition of the present invention is preferably in a range of 0.1 to 15 parts by weight, more preferably in a range of 0.5 to 10 parts by weight per 100 parts by weight of an organic component which is a sum of (a) the hydrophobic polymerizable monomer and (b) the polymer of acidic group-containing polymerizable monomers.

When a content of an acidic group-containing polymerizable monomer is less than 0.1 part by weight, the adherability improving effect is not recognized and, on the other hand, when the content exceeds 15 parts by weight, since an acidic group-containing polymerizable monomer has the worse polymerizability, there is a possibility that polymerization of various polymerizable monomers is inhibited, and the material properties of the cement composition of the present invention are deteriorated.

The (c) hydrophilic polymerizable monomer which is a component contained in a water-based paste constituting the cement composition of the present invention is an essential component for a polymerization reaction in the presence of a polymerization catalyst when a resin-based paste and a water-based paste are mixed, and a polymerizable monomer exhibiting hydrophilicity can be used without any limitation, regardless of a kind of a radically polymerizable unsaturated group, whether monofunctional or polyfunctional.

In addition, the important requirement of the present invention is that a hydrophilic polymerizable monomer is uniformly soluble to water contained in the same water-based paste. Further, as this hydrophilic polymerizable monomer, a monomer which is soluble also to a hydrophobic polymerizable monomer contained a resin-based paste is preferable. This is for rendering easy mixing of a resin-based paste and a water-based paste having entirely different solubilities in water.

Further, by containing a hydrophilic polymerizable monomer in a water-based paste to slightly increase a viscosity of aqueous components, sedimentation or separation of a filler can be controlled when an acid reactive filler is contained. Further, since a hydrophilic polymerizable monomer also has the moisture retaining effect for water, even when a water-based paste containing water is stored under various environments, it has also a role in improving storage stability such as preventing a filler from becoming the powder-coated state due to vaporization of water.

The "hydrophilic polymerizable monomer" referred herein is defined as a polymerizable monomer whose solubility is 10 parts by weight or larger with respect to 100 parts by weight of water at 23° C. Specifically, a polymerizable monomer 10 g is added to 100 g of water at 23° C. in a sample bottle, and they are mixed for 10 minutes. After 10 minutes for standing, the mixture is observed in the bottle. When the mixture is clear or translucent because the monomer dissolves, the polymerizable monomer is considered as a hydrophilic polymerizable monomer.

Examples of a kind of a radically polymerizable unsaturated group possessed by a hydrophilic polymerizable monomer include a (meth)acryloyl group, a styryl group, a vinyl group, and an allyl group and, particularly, it is preferable to use a hydrophilic polymerizable monomer having a (meth)acryloyl group as an unsaturated group.

Further, these hydrophilic polymerizable monomers may also contain an acidic group such as a carboxyl group, a phosphoric acid group, a phosphonic acid group, and a sulfonic acid group, and other functional group such as an alkyl group, halogen, an amino group, a glycidyl group and a hydroxy group in a molecule as far as they exhibit hydrophilicity.

Among hydrophilic polymerizable monomers, examples of a hydrophilic polymerizable monomer having a (meth)acryloyl group as a radically polymerizable unsaturated group include 2-hydroxyethyl(meth)acrylate, 2-hydroxypropyl (meth)acrylate, 3-hydroxypropyl(meth)acrylate, 1,2-dihydroxypropyl(meth)acrylate, 1,3-dihydroxypropyl (meth)acrylate, 2,3-dihydroxypropyl(meth)acrylate, 2-hydroxypropyl-1,3-di(meth)acrylate, 3-hydroxypropyl-1,2-di(meth)acrylate, pentaerythritol di(meth)acrylate, 2-trimethylammonium ethyl(meth)acryl chloride, (meth)acrylamide, 2-hydroxyethyl(meth)acrylamide, and polyethylene glycol di(meth)acrylate (having the number of oxyethylene groups of 9 or more).

The aforementioned hydrophilic polymerizable monomers are not limited to them, and those monomers can be used alone, or by combining a plurality of them.

Among these hydrophilic polymerizable monomers, a hydrophilic polymerizable monomer having solubility in 100 parts by weight of water at 23° C., of 20 parts by weight or more is preferable, and a hydrophilic polymerizable monomer having solubility in 100 parts by weight of water at 23° C., of 40 parts by weight or more is more preferable. Specifically, it is preferable to use 2-hydroxyethyl (meth)acrylate, polyethyleneglycol di(meth)acrylate (the number of oxyethylene groups is 9), polyethyleneglycol di(meth)acrylate (the number of oxyethylene groups is 14), or polyethyleneglycol di(meth)acrylate (the number of oxyethylene groups is 23).

The (d) water which is a component contained in a water-based paste constituting the cement composition of the present invention is an essential component for setting a polymer of acidic group-containing polymerizable monomers by an acid-base reaction with an acid reactive filler, and for acid-base reacting with a metal element such as calcium present in a dentin to manifest adhesion to tooth substance. For this reason, water can be used without any limitation as far as it does not contain impurities adversely affecting on setting of the cement component and adhesion to tooth substance. It is preferable to use distilled water or ion-exchanged water.

The important requirement for manifesting various excellent properties of the cement composition of the present invention is a construction of components contained in a water-based paste and contents thereof, as well as the mixture state of aqueous components contained in a water-based paste.

A water-based paste constituting the cement composition of the present invention does not contain an organic compound having an acidic group, and contains (c) a hydrophilic polymerizable monomer and (d) water which are aqueous components as an essential component and, further, may contain (e) an acid reactive filler, which are inorganic components and (f) a polymerization catalyst.

Among these components, it is the requirement for manifesting various properties which are characteristics of the cement component of the present invention that the hydrophilic polymerizable monomer and water which are aqueous components are soluble to each other.

A content of each component constituting an aqueous component contained in a water-based paste is such that (c) a hydrophilic polymerizable monomer is preferably in a range of 10 to 50 parts by weight, more preferably in a range of 20 to 40 parts by weight per 100 parts by weight of an aqueous component which is a sum of (c) a hydrophilic polymerizable monomer and (d) water.

When a content of a hydrophilic polymerizable monomer is less than 10 parts by weight, since a resin-based paste and a water-based paste have worse miscibility when both are mixed, a mixed material does not become uniform, and the stable material properties can not be obtained. When an acid reactive filler is contained in a water-based paste, there is a possibility that sedimentation or separation of a filler occurs, and water contained in a water-based paste is vaporized, and a filler is brought into the power-coated state.

Thereupon, since a content of water exceeds 90 parts by weight, there is a possibility that an acid-base reaction is delayed, and water sensitivity which is shortcoming of a glass ionomer cement is manifested. Further, since extra water is present, this adversely affects on a polymerization reaction, and the intended material properties can not be obtained.

On the other hand, when a content of a hydrophilic polymerizable monomer exceeds 50 parts by weight, since a content of water is reduced, an acid-base reaction occurs with difficulty, and there is a tendency that adhesion to tooth substance which is the characteristic of a glass ionomer cement is deteriorated.

In order to cause an acid-base reaction by mixing a resin-based paste and a water-based paste constituting the cement composition of the present invention, an acid reactive filler must be contained in at least one of a resin-based paste and a water-based paste, and it is preferable that an acid reactive filler is contained in both of these pastes.

In the present invention, (e) the acid reactive filler can be used without any limitation as far as it acid-base reacts with an acidic group possessed by a polymer of acidic group-containing polymerizable monomers in the presence of water. In order that an acid reactive filler acid-base reacts therewith, an acid reactive element such as metal elements belonging to Periodic Table Group I, Group II and Group III must be contained in an acid reactive filler. Examples of such the acid reactive element are not limited to, but include sodium, potassium, calcium, strontium, lanthanum, and aluminum.

An acid reactive filler may contain one or two or more kinds of these acid reactive elements, and a content thereof is not particularly limited. Further, elements other than these acid reactive elements to be contained in an acid reactive filler are not particularly limited, but an acid reactive filler can contain various elements.

That is, as an acid reactive filler contained in the cement composition of the present invention, oxide, hydroxide, sulfate, nitrate, phosphate, carbonate, silicate, fluoride, nitride, mineral, and glass can be used without any limitation as far as it contains an acid reactive element.

Examples of these acid reactive fillers are not limited to, but include aluminum silicate, aluminum oxide, glass (including a glass obtained by a melting method, a glass produced by a vapor phase reaction, and a synthetic glass obtained by a sol-gel method), strontium fluoride, calcium carbonate, mica, aluminum sulfate, calcium sulfate, barium sulfate, calcium phosphate, calcium hydroxide, strontium hydroxide, zeolite, hydroxyapatite, and aluminum nitride.

These acid reactive fillers exhibiting any property of insolubility, hard solubility or easy solubility in water can be used without any problem. Further, a shape of an acid reactive filler is not particularly limited, but arbitral particle shapes such as spherical, needle-like, plate-like, ground-like, and scaly-shapes can be used without any limitation.

These acid reactive fillers can be used alone, or by combining a few kinds and, when acid reactive fillers are contained in both of a resin-based paste and a water-based paste, respectively, acid reactive fillers may be the same or different, being not particularly problematic.

Since the cement composition of the present invention is required to have many various properties such as fluorine sustained-releasability, radiopacity, transparency and surface curability in addition to adhesion to tooth substance due to an acid-base reaction, it is preferable to use an acid reactive filler which can also manifest those various properties.

Therefore, in order to impart various properties to the cement composition of the present invention, among the aforementioned acid reactive fillers, it is a preferable aspect to use an acid reactive glass filler because a fluorine element and a radiopaque element can be contained, a refractive index of an acid reactive filler can be easily adjusted by controlling a kind of an acid reactive element and other elements contained in an acid reactive filler, and contents thereof, and transparency of the cement composition can be controlled due to lack of a crystalline structure.

These acid reactive glass fillers will be specifically exemplified. Examples include an aluminosilicate glass, borosilicate, aluminoborate, a boroaluminosilicate glass, a phosphate glass, a borate glass and a silica glass containing fluorine as a fluorine releasing element, or containing strontium, lanthanum, zirconium, titanium, yttrium, ytterbium, tantalum, tin, tellurium, tungsten and bismuth as a X-ray shielding element, and containing an acid reactive element, being not limiting. In the present invention, an acid reactive glass filler may contain both of a fluorine releasing element and a X-ray shielding element.

These acid reactive glass fillers can be used alone, or by combining plural of them.

A process for producing these acid reactive glass fillers is not particularly limited, but an acid reactive glass filler produced by any process such as a melting process, a vapor phase process and a sol-gel process can be used without any problem. Inter alia, an acid reactive glass filler produced by a melting process or a sol-gel process which can easily control a kind of an element contained in an acid reactive glass filler and a content thereof is preferably used.

As an acid reactive glass filler, those which are generally sold as a filler can be used without processing such as grinding, but it is preferable to use a filler after ground into a desired average particle diameter. A grinding method is not particularly limited, but a filler obtained by grinding using any of wet or dry grinding methods can be used.

Specifically, examples include a high speed rotating mill such as a hammer mill and a turbo-mill, a container driving medium mill such as a ball mill and a vibration mill, a medium stirring mill such as a sand grinder and attritor, and a jet mill. An average particle diameter of an acid reactive glass filler can be appropriately selected depending on utility or use purpose of the cement composition of the present invention.

For example, when the cement composition of the present invention is used as a material for filling or core construction, since a high mechanical strength is required, an average particle diameter of an acid reactive glass filler is preferably in a range of 0.01 to 30.0 µm, more preferably in a range of 0.01 to 10.0 µm.

In addition, when the cement composition of the present invention is used for cementation, since a thin film thickness is required, an average particle diameter of an acid reactive glass filler is preferably in a range of 0.01 to 10.0 µm, more preferably in a range of 0.01 to 5.0 µm.

When an average particle diameter of an acid reactive glass filler is less than 0.01 µm, since a surface area of a filler is increased, an acid reactive glass filler can not be contained in each paste at a large amount, and there is a possibility that various properties, required in each application, particularly, a mechanical strength is reduced.

Where the filler is used for filling, when an average particle diameter of an acid reactive glass filler exceeds 30.0 μm, a material surface after abrasion becomes rough, a smooth surface which is glassy and has a luster can not be obtained and there is a possibility that coloration or discoloration may be caused. In addition, where the filler is used for cementation, when an average particle diameter of an acid reactive glass filler exceeds 10.0 μm, since a film thickness becomes thick, a prosthesis to be adhered is risen, and intended adaptation of a prosthesis can not be obtained.

As far as an acid-base reaction is not adversely affected, for the purpose of imparting excellent various properties to the cement composition of the present invention or for other purpose, a surface of these acid reactive glass fillers can be treated and multi-functionalized to improve wettability with various polymerizable monomers or water.

A surface of these acid reactive glass fillers can be treated by using a surface treating agent, or other surface treating method.

Examples of a surface treating agent which can be used in surface treatment include a surfactant, fatty acid, an organic acid, an inorganic acid, a silane coupling agent, a titanate coupling agent, and polysiloxane. Examples of the surface treating method which can be used in the present invention include aggregating treatment in which fillers are aggregated in a liquid phase or a vapor phase, and heat-treated thereafter, microcapsulation in which a filler surface is enclosed with an organic substance, and grafting in which a filler surface is functionalized with an organic substance.

The surface treating agent and the surface treating method which can be used in the present invention is not limited to those described above, and these surface treating agents and surface treating methods can be used alone, or by combining them.

Among these surface treating agents and surface treating methods, polysiloxane treatment of coating a surface of an acid reactive glass filler with polysiloxane is a preferable aspect because a reaction rate of an acid-base reaction can be controlled. That is, by polysiloxane treatment, a handling time at mixing a resin-based paste and a water-based paste constituting the cement composition of the present invention and a setting time after mixing can be arbitrarily controlled.

Examples of a silane compound which can be used in this polysiloxane treatment are not limited to, but include tetramethoxysilane, tetraethoxysilane, tetrapropoxysilane, tetraallyloxysilane, tetrabutoxysilane, tetrakis(2-ethylhexyloxy)silane, trimethoxychlorosilane, triethoxychlorosilane, triisopropoxychlorosilane, trimethoxyhydroxysilane, diethoxydichlorosilane, tetraphenoxysilane, tetrachlorosilane, silicon hydroxide (silicon oxide hydrate) and a low condensate of those silane compounds.

Among these silane compounds, tetramethoxysilane, tetraethoxysilane and a low condensate entity of those silane compounds are preferable, and tetramethoxysilane and a low condensate of tetraethoxysilane are more preferable.

These silane compounds can be used alone, or plural of them can be used. Alternatively, an organosilane compound which will be described as a part of a silane compound below may be used.

Further, silane treatment of modifying a surface of an acid reactive filler with an organosilane compound is a preferable aspect because wettability with various polymerizable monomers is enhanced, a content of a filler in each paste is increased, and a material strength of the cement component of the present invention can be enhanced. In addition, this silane treatment can also control a reaction rate of an acid-base reaction like the aforementioned polysiloxane treatment.

Examples of the organosilane compound which can be used in this silane treatment are not limited to, but include methyltrimethoxysilane, ethyltrimethoxysilane, methoxytripropylsilane, propyltriethoxysilane, hexyltrimethoxysilane, vinyltrimethoxysilane, vinyltriethoxysilane, vinyltri(β-methoxyethoxy)silane, γ-methacryloxypropyltrimethoxysilane, γ-glycidoxypropyltrimethoxysilane, γ-mercaptopropyltrimethoxysilane, γ-aminopropyltriethoxysilane, 3-aminopropyltriethoxysilane, methyltrichlorosilane, and phenyltrichlorosilane.

Among these organosiloxane compounds, it is effective to use vinyltrimethoxysilane, vinyltriethoxysilane, vinyltrichlorosilane, vinyl(β-methoxyethoxy)silane, γ-methacryloxypropyltrimethoxysilane, γ-glycidoxypropyltrimethoxysilane, γ-mercaptopropyltrimethoxysilane, and γ-aminopropyltrimethoxysilane while are the compounds known as a silane coupling agent in the dental field, and it is more preferable to use γ-methacryloxypropyltrimethoxysilane.

These organosilane compounds can be used alone, or plural of them may used.

The cement composition of the present invention is characterized in that the composition reduces water sensitivity which is shortcoming of the conventional glass ionomer cement, and has a high level bending strength while it has excellent biocompatibility, adhesion to tooth substance, fluorine sustained-releasability and surface curability possessed by the conventional glass ionomer cement.

In order to manifest these characteristics, by mixing a resin-based paste and a water-based paste constituting the cement composition of the present invention, an acid-based reaction derived from three components of an acid reactive filler, water and a polymer of acidic group-containing polymerizable monomers which are their fundamental constitutional components, and a polymerization reaction derived from various compounds having a polymerizable group and a polymerization catalyst must occur in a balanced manner, thus curing the composition.

For realizing this, an acid reactive filler must be contained in at least one of a resin-based paste and a water-based paste, and it is preferable that an acid reactive filler is contained in both of these pastes.

A content of an acid reactive filler contained in a resin-based paste is in a range of 0 to 50 parts by weight, preferably in a range of 20 to 40 parts by weight per 100 parts by weight of a resin-based paste.

A content of an acid reactive filler contained in a water-based paste is in a range of 0 to 70 parts by weight, preferably in a range of 30 to 55 parts by weight per 100 parts by weight of a water-based paste.

As used herein, a content of each component per 100 parts by weight of a resin-based paste or a water-based paste means such that "100 parts by weight of paste" is a sum of all components containing not only essential components but also optional components. For example, when an acid reactive filler is contained in a resin-based paste, 100 parts by weight of a paste is a sum of a weight of (a) a hydrophobic polymerizable monomer, a weight of (b) a polymer of acidic group-containing polymerizable monomers, and a weight of (e) an acid reactive filler.

In any paste, when a content of an acid reactive filler is increased (when a content exceeds 50 parts by weight in the case of a resin-based paste, or 70 parts by weight in the case of a water-based paste), each paste becomes hard, raising a problem in a handling property, and a problem of that a paste cannot be formed is caused.

On the other hand, in any paste, when a content of an acid reactive filler is decreased, since a ratio of an acid-base reaction occupied in a curing reaction is reduced, there is a possibility that intended characteristics similar to those of a glass ionomer cement cannot be manifested.

Therefore, contents of constitutional components involved in an acid-base reaction including acid reactive filler in the cement component of the present invention, and a ratio of these components to be contained are an important requirement.

A total content of (e) an acid reactive filler, (b) a polymer of acidic group-containing polymerizable monomers and (d) water which are constitutional components causing an acid-base reaction must be in a range of 40 to 90 part by weight per 100 parts by weight of the cement composition of the present invention, and a ratio of these three components to be contained must be in a range of an acid reactive filler: a polymer of acidic group-containing polymerizable monomers:water=1:0.1-2.9:0.1-3.6.

It is more preferable that a total content of the aforementioned three constitutional components (acid reactive filler, polymer of acidic group-containing polymerizable monomer and water) is in a range of 50 to 80 parts by weight per 100 parts by weight of the cement composition of the present invention, and a ratio of these three components to be contained is in a range of an acid reactive filler: a polymer of acidic group-containing polymerizable monomers:water=1:0.2-1.0:0.2-1.0.

When these constitutional components do not satisfy the above condition, this adversely affects on biocompatibility, adhesion to tooth substance, fluorine sustained-releasability and surface curability which are the characteristics similar to those of glass ionomer cement, and a mechanical strength and control of water sensitivity based on a polymerization reaction. That is, when a total content of constitutional components involved in an acid-based reaction exceeds 90 parts by weight, since the cement approaches the conventional glass ionomer cement in terms of physical properties, there is a possibility that shortcoming of water sensitivity possessed by the glass ionomer cement is manifested. On the other hand, when a total content becomes less than 40 parts by weight, since the properties of the cement approach various properties of a resin cement, characteristics of glass ionomer cement can not be manifested.

Also in a ratio of constitutional component to be contained, when each constitutional component is outside a proper range, this becomes a cause for causing a variety of problems.

For example, when a ratio of a polymer of acidic group-containing polymerizable monomers to be contained exceeds 2.9 relative to 1 of an acid reactive filler, since a polymer of acidic group-containing polymerizable monomers having an unreactive acidic group not involved in an acid-base reaction remains at a large amount in a cement composition, a cement composition after curing becomes easy to absorb water, and there is a possibility that reduction in mechanical properties and increase in solubility are caused. On the other hand, when the ratio becomes less than 0.1, an acid-base reaction does not sufficiently occur, and various properties similar to those of a glass ionomer cement can not be obtained.

In addition, when a ratio of water to be contained exceeds 3.6 relative to 1 of an acid reactive filler, since an acid-base reaction is delayed, water sensitivity which is shortcoming of a glass ionomer cement is caused and, at the same time, a polymerization reaction is adversely affected, and there is a possibility that the intended material properties can not be obtained. On the other hand, when the ratio becomes less than 0.1, since a polymer of acidic group-containing polymerizable monomers contained in a resin-based paste can not be dissolved at mixing, an acid-base reaction does not sufficiently occur, leading to a cement component like a resin cement simply containing an acid reactive filler and, therefore, characteristics similar to those of a glass ionomer cement can not be manifested.

In order to cause an acid-base reaction derived from three components of an acid reactive filler, water and a polymer of acidic group-containing polymerizable monomers and, at the same time, a polymerization reaction by mixing a resin-based paste and a water-based paste constituting the cement composition of the present invention, at least one paste of a resin-based paste and a water-based paste constituting the cement composition of the present invention must contain (f) a polymerization catalyst which is a component.

In the present invention, the polymerization catalyst is not particularly limited, and the known radical generator can be used without any limitation. A kind of a polymerization catalyst is roughly classified into a catalyst which initiates polymerization generally by mixing immediately before use (chemical polymerization catalyst), a catalyst which initiates polymerization with light irradiation (photopolymerization catalyst) and a catalyst which initiates polymerization by heating or warming (thermal polymerization catalyst) and these may be used alone, or a combination of plural of them can be used.

Examples of a chemical polymerization catalyst which can be used in the present invention include a redox-type polymerization catalyst system comprising organic peroxide/amine compound, organic peroxide/amine compound/sulfinate, organic peroxide/amine compound/borate compound, and a polymerization catalyst system such as organic boron compounds, perborates, permanganates, and persulfates which initiate polymerization by reacting with oxygen or water. Further, sulfinates, borate compounds and barbituric acids themselves can initiate polymerization in the presence of water or a polymerizable monomer having an acidic group.

Examples of the organic peroxide are not limited to, but include benzoyl peroxide, parachlorobenzoyl peroxide, 2,4-dichlorobenzoyl peroxide, acetyl peroxide, lauroyl peroxide, tertiary butyl peroxide, cumene hydroperoxide, 2,5-dimethylhexane, 2,5-dihydroperoxide, methyl ethyl ketone peroxide, and tertiary butyl peroxybenzoate. The organic peroxides can be used alone, or in a combination of a few of them.

As the amine compound, secondary or tertiary amine in which an amine group is bound to an aryl group is preferable, and examples are not limited to, but include N,N-dimethyl-p-toluidine, N,N-dimethylaniline, N-β-hydroxyethyl-aniline, N,N-di(β-hydroxyethyl)-aniline, N,N-di(β-hydroxyethyl)-p-toluidine, N-methyl-aniline, and N-methyl-p-toluidine. The amine compounds may be used alone, or in combination of a few of them.

Examples of sulfinates are not limited to, but include sodium benzenesulfinate, lithium benzenesulfinate, and sodium p-toluenesulfinate. The sulfinates may be used alone, or in a combination of a few of them.

Examples of the borate compound are not limited to, but include a sodium salt, a lithium salt, a potassium salt, a magnesium salt, a tetrabutylammonium salt, and a tetramethylammonium salt of trialkylphenylboron, and trialkyl(p-fluorophenyl)boron (wherein an alkyl group is a n-butyl group, a n-octyl group, a n-dodecyl group etc.) The borate compounds may be used alone, or in a combination of few of them.

Examples of barbituric acids are not limited to, but include barbituric acid, 1,3-dimethylbarbituric acid, 1,3-diphenylbarbituric acid, 1,5-dimethylbarbituric acid, 5-butylbarbituric acid, 5-ethylbarbituric acid, 5-isopropylbarbituric acid, 5-cyclohexylbarbituric acid, 1,3,5-trimethylbarbituric acid, 1,3-dimethyl-5-ethylbarbituric acid, 1,3-dimethyl-n-butylbarbituric acid, 1,3-dimethyl-5-isobutylbarbituric acid, 1,3-dimethyl-barbituric acid, 1,3-dimethyl-5-cyclopentylbarbituric acid, 1,3-dimethyl-5-cyclohexylbarbituric acid, 1,3-dimethyl-5-phenylbarbituric acid, 1-cyclohexyl-5-ethylbarbituric acid, 1-benzyl-5-phenylbarbituric acid and thiobarbituric acids, and salts thereof (particularly, alkali metals or alkali earth metals are preferable), for example, sodium 5-butylbarbiturate, sodium 1,3,5-trimethylbarbiturate, potassium 1,3,5-trimethylbarbiturate and sodium 1-cyclohexyl-5-ethylbarbiturate. The barbiturates may be used alone, or in a combination of a few of them.

Among these chemical polymerization catalysts, it is preferable to use sulfinates, barbiturates, and organic peroxide/tertiary amine alone or in a combination thereof, and it is more preferable to use salts of barbituric acid or organic peroxide/water-soluble tertiary amine or a combination thereof.

A content of these chemical polymerization catalysts is preferably in a range of 0.1 to 15.0 parts by weight, more preferably in a range of 0.1 to 10.0 parts by weight per 100 parts by weight of each paste. Most preferably, a resin-based paste contains salts of barbituric acid and organic peroxide, and a total content of them is in a range of 0.05 to 8.0 parts by weight, and a water-based paste contains water-soluble tertiary amine, and a content thereof is in a range of 0.01 to 8.0 parts by weight.

Examples of a photopolymerization catalyst which can be used in the present invention include a catalyst consisting only of a photosensitizer system, and a combination of a photosensitizer/photopolymerization promoter.

The photosensitizer is roughly classified into a photosensitizer which initiates polymerization by ultraviolet-ray, and a photosensitizer which initiates polymerization with visible light.

Examples of the photosensitizer which can be used as a photopolymerization catalyst are not limited to, but include α-diketones such as benzil, camphorquinone, α-naphthyl, acetonaphcene, p,p'-dimethoxybenzil, p,p'-dichlorobenzylacetyl, pentanedione, 1,2-phenanthrenequinone, 1,4-phenanthrenequinone, 3,4-phenanethrenequinone, 9,10-phenanthrenequinone, and naphthoquinone, benzoin alkyl ethers such as benzoin, benzoin methyl ether, and benzoin ethyl ether, thioxanthones such as thioxanthone, 2-chlorothioxanthone, 2-methylthioxanthone, 2-isopropylthioxanthone, 2-methoxythioxanthone, 2-hydroxythioxanthone, 2,4-diethylthioxanthone, and 2,4-diisopropylthioxanthone, benzophenones such as benzophenone, acetoinbenzophenone, p-chlorobenzophenone, and p-methoxybenzophenone, acylphosphine oxides such as 2,4,6-trimethylbenzoyldiphenylphosphine oxide, and bis(2,6-dimethoxybenzoyl)-2,4,4-trimethylpentylphosphine oxide, α-aminoacetophenones such as 2-benzyl-dimethylamino-1-(4-morpholinophenyl)-butanone-1,2-benzyl-diethylamino-1-(4-morpholinophenyl)-propanone-1, ketals such as benzyldimethylketal, benzyldiethylketal, and benzyl(2-methoxyethylketal), and titanocenes such as bis(cyclopentadienyl)-bis[2,6-difluoro-3-(1-pyrrolyl)phenyl]-titanium, bis(cyclopentadienyl)-bis(pentanefluorophenyl)-titanium, and bis(cyclopentadienyl)-bis(2,3,5,6-tetrafluoro-4-disiloxyphenyl)-titianium, the photosensitizers may be used alone or in a combination of a few of them.

Examples of the photopolymerization promoter which can be used as the photopolymerization catalyst are not limited to, but include tertiary amines such as N,N-dimethylaniline, N,N-diethylaniline, N,N-di-h-butylaniline, N,N-dibenzylaniline, N,N-dimethyl-p-toluidine, N,N-dimethyl-m-toluidine, N,N-diethyl-p-toluinine, p-bromo-N,N-dimethylaniline, m-chloro-N,N-dimethylaniline, p-dimethylaminobenzaldehyde, p-dimethylaminoacetophenone, p-dimethylaminobenzoic acid, p-dimethylaminobenzoic acid ethyl ester, p-dimethylaminobenzoic acid amino ester, N,N-dimethylanthranilic acid methyl ester, N,N-dihydroxyethylaniline N,N-dihydroxyethyl-p-toluidine, p-dimethylaminophenyl alcohol, p-dimethylaminostyrene, N,N-dimethyl-3,5-xylidine, 4-dimethylaminopyridine, N,N-dimethyl-α-naphthylamine, N,N-dimethyl-β-naphthylamine, tributylamine, tripropylamine, triethylamine, N-methyldiethanolamine, N-ethyldiethanolamine, N,N-dimethylhexylamine, N,N-dimethyldodecylamine, N,N-dimethylstearylamine, N,N-dimethylaminoethyl acrylate, N,N-diethylaminoethyl methacrylate, and 2,2'-(N-butylimino)diethanol, secondary amines such as N-phenylglycine, barbituric acids such as 5-butylbarbituric acid, 1-benzyl-5-phenylbarbital, 1,3,5-trimethylbarbituric acid, sodium 1,3,5-trimethylbarbiturate, and potassium 1,3,5-trimetylbarbiturate, tin compounds such as dibutyltin diacetate, dibutyltin laurate, dioctyltin dilaurate, dioctyltin diversatate, dioctyltin bis(mercaptoacetic acid isooctyl ester) salt, and tetramethyl-1,3-diacetoxy distannoxane, aldehyde compounds such as lauryl aldehyde, and terephthalaldehyde, and sulfur compounds such as dodecylmercaptan, 2-mercaptobenzooxazole, 1-decanethiol and thiosalicylic acid. The photopolymerization promoters may be used alone, or in a combination of a few of them.

Further, in order to improve the photopolymerization promoting ability, it is effective to add oxycarboxylic acids such as citric acid, malic acid, tartaric acid, glycolic acid, glucuronic acid, α-oxyisobutyric acid, 2-hydroxypropanoic acid, 3-hydroxypropanoic acid, 3-hydroxybutanoic acid, 4-hydroxybutanoic acid and dimethylolpropionic acid in addition to the aforementioned photopolymerization promoters.

In addition, among photopolymerization catalysts, a combination of α-diketone and tertiary amine or α-diketone and tin compounds is preferable, and a combination of camphorquinone and aromatic tertiary amine in which an amino group is directly bound to a benzene ring such as ethyl p-N,N-dimethylaminobenzoate, or aliphatic tertiary amine having a double bond in a molecule such as N,N-dimethylaminoethyl methacrylate, and a combination of camphorquinone and tin compounds such as dibutyltin dilaurate and dioctyltin dilaurate are more preferable.

A content of these photopolymerization catalysts is preferably in a range of 0.1 to 15.0 parts by weight, more preferably in a range of 0.1 to 10.0 parts by weight per 100 parts by weight of each paste. Most preferably, a content of these photopolymerization catalysts is in a range of 0.1 to 8.0 parts by weight per 100 parts by weight of each paste.

As the thermal polymerization catalyst which can be used in the present invention, in addition to the organic peroxide, azo compounds such as azobisisobutyronitrile, methyl azobisisobutyrate, and azobiscyanovaleric acid are preferably used, being not limiting. These thermal polymerization catalysts may be used alone, or in a combination of a few of them.

Further, depending on application, sensitizing dyes such as coumarin series, cyanine series, and thiazine series, light acid generators, which produce a Brønsted acid or Lewis acid by irradiating a halometyl group substituted-s-triazine derivative or a diphenyl iodonium salt compound with light, quaternary ammonium halides and transition metal compounds can be appropriately used.

Polymerization catalysts which can be used in the cement composition of the present invention can be used alone or by combining plural of them, depending on application or use purpose of the cement composition of the present invention, regardless of a polymerization form and a kind of a polymerization catalyst.

For example, when the cement composition of the present invention is used in application such as cementation of inlay or a crown which in a metal prothesis material, and root canal filling, since it is difficult to perform sufficient light irradiation, it is preferable to use a chemical polymerization catalyst with an acid-base reaction.

On the other hand, when the cement composition of the present invention is used in application such as filling into a cavity after caries treatment or a sealant, since sufficient light irradiation can be performed, it is preferable to use a photopolymerization catalyst or both of a photopolymerization catalyst and a chemical polymerization catalyst with an acid-base reaction.

The cement composition of the present invention can contain other components in addition to the aforementioned constitutional components (a) to (g) to such an extent that various properties of the cement composition of the present invention are not affected.

In order to impart adherability for a noble metal to the cement composition of the present invention, it is also effective that a polymerizable monomer containing a sulfur atom in a molecule is contained in any one of a resin-based paste and a water-based paste constituting the cement composition of the present invention. A polymerizable monomer containing a sulfur atom in a molecule can be used regardless of a kind and the number of an unsaturated group and the presence or the absence of other functional group.

Examples of a polymerizable monomer containing a sulfur atom in a molecule having a (meth)acryloyl group as an unsaturated group are not limited to, but include (meth)acrylate having a triazinethiol group, (meth)acrylate having a mercapto group, (meth)acrylate having a polysulfide group, (meth)acrylate having a thiophosphoric acid group, (meth)acrylate having a disulfide ring group, (meth)acrylate having a marcaptodiathiazole group, (meth)acrylate having a thiouracil group, and (meth)acrylate having a thiirane group. These polymerizable monomers containing a sulfur atom in a molecule may be used alone, or in a combination of plural of them.

A content of this polymerizable monomer containing a sulfur atom in a molecule can be appropriately selected depending on application, use purpose or use method of the cement composition of the present invention, and it is preferable that the content is in a range of 1.0 to 8.0 parts by weight per 100 parts by weight of each paste in a resin-based paste and/or a water-based paste into which a polymerizable monomer containing a sulfur atom is contained. When a content of the polymerizable monomer containing a sulfur atom in a molecule exceeds 10.0 parts by weight, since this inhibits an acid-base reaction or a polymerization reaction, there is a possibility that various intended properties are adversely affected. On the other hand, when the content of this polymerizable monomer is less than 0.1 part by weight, sufficient adherability for a noble metal can not be obtained.

For the purpose of delaying a curing reaction consisting of an acid-base reaction or a polymerization reaction caused by mixing a resin-based paste and a water-based paste constituting the cement composition of the present invention, an organic solvent can be contained in any one of a resin-based paste and a water-based paste such an extent that various properties are not adversely affected. Further, for the purpose of adjusting viscosities of both pastes to the same extent to improve a mixing property, an organic solvent may be contained as a viscosity adjusting agent.

Examples of such the organic solvent are not limited to, but include alcohols such as methanol, ethanol, 1-propanol, 2-propanol, and 1-butanol, ether compounds such as triethylene glycol monomethyl ether, triethylene glycol monoethyl ether, dipropylene glycol monomethyl ether, tetrahydrofuran, and dimethoxyethane, and ketone compounds such as acetone, and methyl ethyl ketone. These organic solvents may be used alone or in a combination of a few of them.

Among these organic solvents, methanol, ethanol, 1-propanol, 2-propanol, and acetone which are water-soluble organic solvents are preferable, and acetone and ethanol are more preferable.

A content of these organic solvents can be appropriately selected depending on application, use purpose, or use method of the cement composition of the present invention, and it is preferable that the content is in a range of 1.0 to 8.0 parts by weight per 100 parts by weight of each paste in a resin-based paste and/or a water-based paste into which an organic solvent is contained.

When a content of an organic solvent exceeds 8.0 parts by weight, there is a possibility that a curing reaction consisting of an acid-base reaction or a polymerization reaction is delayed too much, and deterioration in various properties is caused. On the other hand, when a content of an organic solvent is less than 1.0 part by weight, the effect on delay of a curing reaction and adjustment of a viscosity in various pastes is not recognized.

In the present invention, a second filler other than an acid reactive filler may be contained in a resin-based paste and a water-based paste or either of them.

A second filler, a filler which does not acid-base-react with a polymer of acidic group-containing polymerizable monomers in the presence of water can be used without any limitation. Examples of the second filler include fillers which are known as a dental filler such as inorganic fillers, organic fillers and organic-inorganic complex fillers, and these can be used alone or in a combination of a few of them without any limitation. In addition, the shape of these second fillers is not particularly limited, but may be an arbitral particle shapes such as spherical, needle-like, plate-like, ground-like, and scaly shapes.

Examples of the inorganic filler are not limited, but include quartz, amorphous silica, ultrafine particulate silica, various glasses not containing an acid reactive element (including glasses obtained by a melting method, synthetic glasses obtained by a sol-gel method, and glasses produced by a vapor phase reaction), silicon nitride, silicon carbide, and boron carbide.

An average particle diameter of these inorganic fillers is not particularly limited, but is preferably in a range of 0.001 to 10 μm, more preferably in a range of 0.01 to 5 μm.

Among the inorganic fillers, since Aerosil which is ultrafine particulate silica produced by a vapor phase method, and a silica-zirconia oxide particle which is an ultrafine particulate silica complex particle produced in a solution of a sol-gel reaction serve as a thickener when contained in a resin-based paste or a water-based paste, they are effective in the present invention.

Examples of Aerosil include Aerosil 200, Aerosil OX50, Aerosil R972, Aerosil R974, Aerosil R8200, Aerosil R711, Aerosil DT4, aluminum oxide C, and titanium dioxide P25. Alternatively, an aggregating inorganic filler in which second fillers containing those ultrafine particles have been intentionally aggregated may be used without any problem.

As the organic filler, any organic filler can be used without any limitation, as far as it is an organic filler obtained by polymerizing a monomer having a polymerizable group, and a kind thereof is not particularly limited. Examples of the organic filler include organic fillers obtained by polymerizing unsaturated aromatic compounds such as styrene, α-methylstyrene, halogenated styrene, and divinylbenzene, unsaturated esters such as vinyl acetate, and vinyl propionate, unsaturated nitriles such acrylonitrile, butadiene, and isoprene alone or copolymerizing a few kinds of them. Particularly preferable are organic fillers obtained by polymerizing various polymerizable monomers which have been already known and used in the dental field.

A process for preparing the organic filler is not particularly limited, and any process such as emulsion polymerization, suspension polymerization and dispersion polymerization of a polymerizable monomer may be used. Alternatively, a method of grinding a previously produced polymer bulk may be used.

An average particle diameter of these organic fillers is preferably in a range of 1 to 100 µm, more preferably in a range of 3 to 50 µm, further preferably in a range of 5 to 30 µm.

Alternatively, an organic-inorganic complex filler having a structure in which inorganic particles are enclosed in an organic polymer may be used. The inorganic filler to be enclosed in an organic polymer is not particularly limited, and known organic fillers can be used. For example, the aforementioned inorganic fillers which can be used as a second filler can be used.

Further, in the organic-inorganic complex filler, since an inorganic filler is enclosed in an organic polymer, the aforementioned acid reactive fillers may be used as an inorganic filler to be contained in the organic-inorganic complex filler as far as it does not acid-base react with a polymer of acidic group-containing polymerizable monomers in the presence of water.

A process for preparing an organic-inorganic complex filler is not particularly limited, but any process can be adopted. Examples include a process of microcapsulating or grafting a surface of an inorganic filler with an organic substance, a process of introducing a polymerizable functional group or a polymerizable initiating group into a surface of an inorganic filler, and radical-polymerizing an organic monomer on the surface, and a process of grinding an organic polymer bulk containing a previously produced inorganic filler.

An average particle diameter of these organic-inorganic complex fillers is preferably in a range of 1 to 100 µm, more preferably in a range of 3 to 50 µm, further preferably in a range of 5 to 30 µm.

In the cement composition of the present invention, a surface of each of an inorganic filler, an organic filler, and an organic-inorganic complex filler used as a second filler can be treated and multi-functionalized to improve wettability between a second filler and various polymerizable monomers or water.

A surface of a second filler can be treated by use of a surface treating agent, or other surface treating method. Examples of the surface treating agent which can be used in surface treatment are not limited to, but include a surfactant, fatty acid, an organic acid, an inorganic acid, a silane coupling agent, a titanate coupling agent, and polysiloxane. A surface treating method which can be used in surface treatment is not particularly limited, but the known methods can be used.

These surface treating agents and surface treating methods can be used alone, or in a combination thereof.

A content of a second filler which is contained in a resin-based paste and/or a water-based paste constituting the cement composition of the presents invention can be arbitrarily set depending on the requirement for the material properties required in the cement composition of the present invention, and is preferably in a range of 1.0 to 50.0 parts by weight per 100 parts by weight of each paste in a resin-based paste and/or a water-based paste into which a second filler is contained.

Where an acid reactive filler is contained in a water-based paste, when inclusion of only a hydrophilic polymerizable monomer is insufficient in the effect on prevention or control of sedimentation of a filler, or the moisture retaining effect, a water-soluble thickener may be contained to such an extent that various properties of the cement composition of the present invention are not influenced.

This water-soluble thickener is not particularly limited, but any of inorganic series and organic series may be used. Examples include potassium carboxymethylcellulose, sodium carboxymethylcellulose, starch, sodium starch glycolate, sodium starch phosphate ester, methylcellulose, polysodium acrylate, alginic acid, sodium alginate, alginic acid propylene glycol ester, casein, sodium caseinate, polyethylene glycol, ethylcellulose, hydroxyethylcellulose, gluten, locust bean gum, and gelatin. Among them, since the viscosity increasing effect is high even at a small amount, and the price is low, potassium carboxymethylcellulose and sodium carboxymethylcellulose are preferable.

These water-soluble thickeners can be used alone, or by mixing two or more kinds. A content of these water-soluble thickeners contained in a water-based paste constituting the cement composition of the present invention is preferably in a range of 0.001 to 1 part by weight per 100 parts by weight of a water-based paste. In order that various properties of the cement composition of the present invention are not adversely affected, the content is more preferably in a range of 0.001 to 0.1 part by weight.

Further, where inclusion of only a hydrophilic polymerizable monomer contained in a water-based paste affords deteriorated miscibility (mixing manner) when a water-based paste and a resin-based paste are mixed, a surfactant can be contained in a resin-based paste and/or a water-based paste to such an extent that various properties of the cement composition of the present invention are not influenced.

The surfactant which can be used in the cement composition of the present invention may be any of an ionic surfactant and a nonionic surfactant.

Examples of the anionic surfactant in the ionic surfactant include aliphatic carboxylic acid metal salts such as sodium stearate, sulfated aliphatic carboxylic acid metal salts such as sodium dioctyl sulfosuccinate, and metal salts of higher alcohol sulfate ester such as sodium stearyl sulfate. In addition, examples of the cationic surfactant include an aduct of higher alkylamine and ethylene oxide, amines made from lower amine, and alkyltrimethylammonium salts such as lauryltrimethylammoniun chloride and, further, examples of the amphoteric surfactant include metal salts of higher alkylaminopropionic acid such as sodium stearylaminopropionate, and betaines such as lauryldimethylbetaine.

Examples of the nonionic surfactant include polyethylene glycol type and polypropylene glycol type in which ethylene oxide or propylene oxide is added to higher alcohols, alkyl phenols, fatty acids, higher fatty amines, or aliphatic amides, and polyhydric alcohol type, a representable which is polyhydric alcohols, diethanolamines, and saccharides.

The aforementioned surfactants are not limited to these, but can be used without any limitation. These surfactants can be used alone, or in a combination of a few kinds.

A content of the surfactant contained in a resin-based paste and/or a water-based paste constituting the cement composition of the present invention is preferably in a range of 0.001 to 5.0 parts by weight per 100 parts by weight of each paste in a resin-based paste and/or a water-based paste into which a surfactant is contained.

In addition, a resin-based paste or a water-based paste constituting the cement composition of the present invention may contain components such as ultraviolet absorbing agent such as 2-hydroxy-4-methylbenzophenone, a polymerization inhibitor such as hydroquinone, hydroquinone monomethyl ether, and 2,5-ditertiary butyl-4-methylphenol, a discoloration preventing agent, an antibacterial agent, a coloring pigment and other previously known additives, if necessary.

The cement composition of the present invention itself has adherability to tooth substance and, when this adherability is enhanced, or when adhered to a material to be adhered other than tooth substance such as a ceramic, a noble metal, and the composite resin, the composition can be used by appropriately combining with other treating agent or a bonding agent such as an etching agent, a primer, a bonding agent, a self etching primer, a ceramic primer, a metal primer, and a noble metal primer.

Since the cement composition of the present invention is constructed of a resin-based paste and a water-based paste, a packaging for the cement composition of the present invention is a packaging form divided into two. However, the cement composition of the present invention may be a packaging form divided into three or more without any limitation, depending on storage stability of the cement composition of the present invention, a ratio of components to be incorporated into the cement composition of the present invention, a kind, a use method and use purpose of a polymerization catalyst.

A weight ratio of mixing a resin-based paste and a water-based paste constituting the cement composition of the present invention can be arbitrarily set depending on utility and use purpose of the cement composition of the present invention and, in order to cause an acid-base reaction and a polymerization reaction in a better balanced manner, it is preferable that a weight reaction of mixing a resin-based paste: an aqueous past is in a range of 0.5:2.0-1.5:0.5.

EXAMPLES

The present invention will be specifically explained below by way of Preparation Examples, Examples and Comparative Examples, but the present invention is not limited to them.

Preparation Example 1

Preparation of Polymer (B-1) of Acidic Group-Containing Polymerizable Monomer

A mixture of 50 g of acrylic acid, 2.5 g of ammonium persulfate, and 80 g of water was added dropwise to a 1 L flask containing 100 g of isopropyl alcohol through an addition funnel at 90° C. under the nitrogen atmosphere, and polymerization was completed in 5 hours. A weight average molecular weight of this acrylic acid polymer was GPC-analyzed by high performance liquid chromatography (GPC-900 manufactured by JASCO Corporation: column GF-510HQ manufactured by SHOWA DENKO K.K.) and, as a result, a weight average molecular weight was found to be 45000. After isopropyl alcohol contained in this acrylic acid polymer solution was replaced with water to prepare a 10% aqueous acrylic acid polymer solution, and this was spray dried to obtain an acrylic acid polymer powder. This acrylic acid polymer powder was dried in vacuum, ground with a mortar, and sifted using a JIS standard sieve (125 mesh and 250 mesh), and a powder passing through a 125 mesh sieve but not passing through a 250 mesh sieve was adopted as a polymer (B-1) of an acidic group-containing polymerizable monomer.

Preparation Example 2

Preparation of Polymer (B-2) of Acidic Group-Containing Polymerizable Monomer

A mixture of 25 g of acrylic acid, 25 g of 3-butene 1,2,3-tricarboxylic acid, 2.5 g of ammonium persulfate, and 80 g of water was added dropwise to a 1 L flask containing 100 g of isopropyl alcohol at 90° C. under the nitrogen atmosphere, and polymerization was completed in 5 hours. A weight average molecular weight of this acrylic acid-3-butene 1,2,3-tricarboxylic acid copolymer was GPC-analyzed by high performance liquid chromatography (GPC-900 manufactured by JASCO Corporation: column GF-510 HQ manufactured by SHOWA DENKO K.K.) and, as a result, a weight average molecular weight was found to be 53000. Isopropyl alcohol contained in this acrylic acid-3-butene 1,2,3-tricarboxylic acid copolymer solution was replaced with water to prepare a 10% aqueous acrylic acid-3-butene 1,2,3-tricarboxylic acid copolymer solution, and this was spray dried to obtain an acrylic acid-3-butene 1,2,3-tricarboxylic acid copolymer powder. This acrylic acid-3-butene 1,2,3-tricarboxylic acid copolymer powder was dried in vacuum, ground with a mortar, and sifted using a JIS standard sieve (125 mesh and 250 mesh), and a powder passing through a 125 mesh sieve but not passing through a 250 mesh sieve was adopted as a polymer (B-2) of an acidic group-containing polymerizable monomer.

Preparation Example 3

Preparation of Acid Reactive Filler (E-1)

Each raw material was sufficiently mixed at a ratio of 29% by weight of silica, 5% by weight of aluminum oxide, 17% by weight of aluminum phosphate, 20% by weight of aluminum fluoride, and 29% by weight of strontium carbonate, the mixture was melted in an Elema furnace at a high temperature of 1350° C., and the melt was cooled to obtain a glass. The glass was ground using a ball mill, and a medium stirring mill, and an acid reactive filler was obtained (E-1).

This acid reactive filler (E-1) was subjected to particle size measurement (Micro Track HRA manufactured by NIKKISO CO., LTD.) and fluorescent X-ray analysis (ZSX100e manufactured by Rigaku Industrial Corporation). As a result, an average particle diameter of an acid reactive filler (E-1) was 2.5 μm, and it was recognized that strontium and aluminum were contained in an acid reactive filler (E-1) as an acid reactive element.

Preparation Example 4

Preparation of Acid Reactive Filler (E-2)

Each raw material was sufficiently mixed at a ratio of 23% by weight of silica, 8% by weight of aluminum oxide, 13% by weight of aluminum phosphate, 14% by weight of aluminum fluoride, and 42% by weight of strontium carbonate, the mixture was melted in an Elema furnace at a high temperature of 1350° C., and the melt was cooled to obtain a glass. The glass was ground using a ball mill and a medium stirring mill, and an acid reactive filler was obtained (E-2).

This acid reactive filler (E-2) was subjected to particle size measurement (Micro Track HRA manufactured by NIKKISO CO., LTD.) and fluorescent X-ray analysis (ZSX100e manufactured by RIGAKU Industrial Corporation). As a result, an average particle diameter of an acid reactive filler (E-2) was 2.3 μm, and it was recognized that strontium and aluminum were contained in an acid reactive filler (E-2) as an acid reactive element.

Preparation Example 5

Preparation of Resin-Based Paste or Water-Based Paste Constituting Cement Composition According to formulation shown in Table 1 or Table 2, a resin-based paste (RP01-15) and a water-based paste (WP01-08) were prepared, respectively, and these were used in Examples and Comparative Examples.

Abbreviations for materials used in preparing a resin-based paste or a water-based paste are as follows:

Bis-GMA: 2,2-bis(4-(3-methacryloyloxy-2-hydroxypropoxy)phenyl)propane

D-2.6E: 2,2-bis(4-methacryloyloxyethoxyphenyl)propane

UDMA: di(methacryloyloxy)-2,2,4-trimethylhexamethylenediurethane

TEGDMA: triethyleneglycol dimethacrylate
2-HENA: 2-hydroxyethyl methacrylate
PG: polyethyleneglycol dimethacrylate (the number of oxyethylene groups is 14)
BPO: benzoyl peroxide
BCa: calcium trimethylbarbiturate
p-TsNa: sodium p-toluenesulfinate
CQ: camphorquinone
6-MHPA: (6-methacryloxy)hexyl phosphonoacetate
4-META: 4-methacryloyloxyethyltrimellitic anhydride
DEPT: N,N-di(β-hydroxyethyl)-p-toluidine
Yv-Si: 10% silane-treated fused silica
R-972: Aerosil R-972

Among the prepared resin-based pastes, RP01-12 are in the state where organic components containing (b) a polymer of acidic group-containing polymerizable monomers are insoluble. RP13 and 14 are in the state where organic components containing (b) a polymer of acidic group-containing polymerizable monomers are soluble to each other. In RP15, (b) a polymer of acidic group-containing polymerizable monomers which is an essential component is not contained in organic components.

On the other hand, among the prepared water-based-pastes, WP01-07 are in the state where aqueous components are soluble, but in WP08, (d) water which is an essential component is not contained in aqueous components.

TABLE 1

Formulation of Resin-Based Paste Constituting Cement Compositions

| | | | Composition No. of Resin-Based Paste | | | | | | | | | | | | | |
|---|---|---|---|---|---|---|---|---|---|---|---|---|---|---|---|---|
| | | | RP01 | RP02 | RP03 | RP04 | RP05 | RP06 | RP07 | RP08 | RP09 | RP10 | RP11 | RP12 | RP13 | RP14 | RP15 |
| Organic Component | Component (a) Hydrophobic Polymerizable Monomer | Bis-GMA | | 24.0 | | | | | | | | | | | 22.8 | | 10.0 | |
| | | D-2.6E | | | 28.0 | | 25.9 | | | | | | | | | | | |
| | | UDMA | 28.0 | | | 25.9 | | 28.0 | 28.0 | 28.0 | 28.0 | 28.0 | 28.0 | | | | | 28.0 |
| | | TEGDMA | 12.0 | 16.0 | 12.0 | 11.1 | 11.1 | 12.0 | 12.0 | 12.0 | 12.0 | 12.0 | 12.0 | 15.2 | | | | 12.0 |
| | Hydrophobic Polymerizable Monomer | 2-HEMA | | | | | | | | | | | | 2.0 | 50.0 | 40.0 | |
| | Component (b) Polymer of Acidic Group-Containing Polymerizable Monomer | B-1 | 25.0 | 25.0 | 25.0 | 25.0 | 25.0 | | 25.0 | 25.0 | 25.0 | 25.0 | 25.0 | 25.0 | 25.0 | 20.0 | |
| | | B-2 | | | | | | 25.0 | | | | | | | | | |
| | Component (g) Acidic Group-Containing Polymerizable Monomer | 6-MHPA | | | | 3.0 | | | | | | | | | | | |
| | | 4-META | | | | | 3.0 | | | | | | | | | | |
| | Mixture state | | Inso. | Inso. | Inso. | Inso. | Inso. | Inso. | Inso. | Inso. | Inso. | Inso. | Inso. | Inso. | Sol. | Sol. | — |
| Component (e) Acid Reactive Filler | | E-1 | 34.0 | 34.0 | 34.0 | 34.0 | 34.0 | 34.0 | 34.0 | 34.0 | 34.0 | | 34.0 | 34.0 | | | 59.0 |
| | | E-2 | | | | | | | | | | | | | 25.0 | 25.0 | |
| Component (f) Polymerizing Catalyst | | BPO | 0.1 | 0.1 | 0.1 | 0.1 | 0.1 | 0.1 | | 0.1 | 0.1 | 0.1 | | 0.1 | 0.1 | 0.1 | 0.1 |
| | | BCa | 0.3 | 0.3 | 0.3 | 0.3 | 0.3 | 0.3 | 0.3 | | 0.3 | 0.3 | | 0.3 | 0.3 | 0.3 | 0.3 |
| | | p-TsNa | | | | | | | | 0.3 | | | | | | | |
| | | CQ | | | | | | | | | | | 0.3 | | | | |
| Second Filler | | Yv-Si | | | | | | | | | | | 34.0 | | | | |
| | | R-972 | 1.0 | 1.0 | 1.0 | 1.0 | 1.0 | 1.0 | 1.0 | 1.0 | 1.0 | 1.0 | 1.0 | 1.0 | | | 1.0 |

Sol.: Soluble,
Inso.: Insoluble

TABLE 2

Formulation of Water-Base Paste Constituting Cement Components

| | | | Composition No. of Water-Based Paste | | | | | | | |
|---|---|---|---|---|---|---|---|---|---|---|
| | | | WP01 | WP02 | WP03 | WP04 | WP05 | WP06 | WP07 | WP08 |
| Aqueous Components | Component (c) Hydrophilic Polymerizable Monomer | 2-HEMA | | 6.0 | 12.0 | | | | | |
| | | PG | 12.0 | 6.0 | | 12.0 | 25.0 | 12.0 | 12.0 | 40.0 |
| | Compound (d) Water | | 30.0 | 30.0 | 30.0 | 30.0 | 10.0 | 30.0 | 30.0 | |
| | Mixture stats | | Sol. | Sol. | Sol. | Sol. | Sol. | Sol. | Sol. | — |
| Component (e) Acid Reactive Filler | | E-1 | 50.0 | 50.0 | 50.0 | 50.0 | 18.0 | | | 52.0 |
| | | E-2 | | | | | | | 50.0 | |
| Component (f) Polymerizing Catalyst | | DEPT | 0.1 | 0.1 | 0.1 | | 0.1 | 0.1 | 0.1 | 0.1 |
| Second Filler | | Yv-Si | | | | | 39.0 | 50.0 | | |
| | | R-972 | 8.0 | 8.0 | 8.0 | 8.0 | | 8.0 | 8.0 | 8.0 |

Sol.: Soluble,
Inso. : Insoluble

Examples 1-12

A resin-based paste (RP01-09 and 12) shown in Table 1 and a water-based paste (WP01-04) shown in Table 2 were mixed at a ratio of a mixing weight ratio of 1.0 g (RP): 1.3 g (WP) in a combination shown in Table 3, to prepare cement compositions 1-12. As shown in Table 3, contents and a ratio of constitutional components involved in an acid-base reaction in these cement compositions 1-12 to be contained are in an optimal range.

Since a cement composition 12 contains a photopolymerization catalyst in a composition, this is an example in which the content composition has a photopolymerization reaction as a curing mechanism in addition to a curing mechanism (an acid-base reaction and a chemical polymerization reaction) possessed by cement compositions 1-11.

A cement composition 13 is an example in which a resin-based paste RP15 not containing (b) a polymer of acidic group-containing polymerizable monomers is used.

A cement composition 14 is an example in which a resin-based paste RP10, and a water-based paste WP06 not containing (e) an acid reactive filler are used.

A cement composition 15 is an example in which a water-based paste WP06 not containing (d) water is used.

A cement composition 16 is an example in which a resin-based paste RP11, and a water-based paste WP04 not containing (f) a polymerization catalyst are used.

A cement composition 17 is an example in which since a resin-based paste RP13 contains a hydrophilic polymerizable monomer instead of a hydrophobic polymerizable monomer as an organic component, (b) a polymer of acidic group-containing polymerizable monomers as an organic component is soluble. A cement composition 18 is an example in which since a resin-based paste RP14 contains a hydrophilic polymerizable monomer in addition to hydrophobic polymerizable monomer as an organic component, (b) a polymer of acidic group-containing polymerizable monomers as an organic component is soluble.

TABLE 3

Formulations of Two Paste Type Glass Ionomer Cement of the Present Invention

|  | Cement Composition | Resin-Based Paste | Water-Based Paste | Weight Ratio RP/WP (g/g) | Content in Cement Composition (Weight %) | Components Involved in Acid-Base Reaction Content Ratio (e):(b):(d) |
|---|---|---|---|---|---|---|
| Ex. 1 | 1 | RP01 | WP01 | 1.0/1.3 | 71 | 1.00:0.25:0.39 |
| Ex. 2 | 2 | RP02 | WP01 | 1.0/1.3 | 71 | 1.00:0.25:0.39 |
| Ex. 3 | 3 | RP03 | WP01 | 1.0/1.3 | 71 | 1.00:0.25:0.39 |
| Ex. 4 | 4 | RP04 | WP01 | 1.0/1.3 | 71 | 1.00:0.25:0.39 |
| Ex. 5 | 5 | RP05 | WP01 | 1.0/1.3 | 71 | 1.00:0.25:0.39 |
| Ex. 6 | 6 | RP03 | WP02 | 1.0/1.3 | 71 | 1.00:0.25:0.39 |
| Ex. 7 | 7 | RP03 | WP03 | 1.0/1.3 | 71 | 1.00:0.25:0.39 |
| Ex. 8 | 8 | RP06 | WP01 | 1.0/1.3 | 71 | 1.00:0.25:0.39 |
| Ex. 9 | 9 | RP07 | WP04 | 1.0/1.3 | 71 | 1.00:0.25:0.39 |
| Ex. 10 | 10 | RP08 | WP01 | 1.0/1.3 | 71 | 1.00:0.25:0.39 |
| Ex. 11 | 11 | RP12 | WP01 | 1.0/1.3 | 71 | 1.00:0.25:0.39 |
| Ex. 12 | 12 | RP09 | WP01 | 1.0/1.3 | 71 | 1.00:0.25:0.39 |

Comparative Examples 1-6

A resin-based paste (RP01, 10, 11 and 13-15) shown in Table 1, and a water-based paste (WP01, 04 and 06-08) shown in Table 2 were mixed at a ratio of a mixing weight ratio of 1.0 g (RP); 1.3 g (WP) in a combination shown in Table 4, to prepare cement compositions 13-18.

TABLE 4

Formulations of Two Paste Type Glass Ionomer Cement in Comparative Examples and Reference Examples

|  | Cement Composition | Resin-Based Paste | Water-Based Paste | Weight Ratio RP/WP (g/g) | Content in Cement Composition (Weight %) | Components Involved in Acid-Base Reaction Content Ratio (e):(b):(d) |
|---|---|---|---|---|---|---|
| Comp. Ex. 1 | 13 | RP15 | WP01 | 1.0/1.3 | 71 | 1.00:0:0.31 |
| Comp. Ex. 2 | 14 | RP10 | WP06 | 1.0/1.3 | 28 | 0.00:∞:∞ |
| Comp. Ex. 3 | 15 | RP01 | WP08 | 1.0/1.3 | 55 | 1.00:0.25:0.00 |
| Comp. Ex. 4 | 16 | RP11 | WP04 | 1.0/1.3 | 71 | 1.00:0.25:0.39 |
| Comp. Ex. 5 | 17 | RP13 | WP07 | 1.0/1.3 | 67 | 1.00:0.28:0.43 |
| Comp. Ex. 6 | 18 | RP14 | WP07 | 1.0/1.3 | 69 | 1.00:0.20:0.39 |
| Ref. Ex. 1 | HY-Bond Glass Ionomer Cement CX | | | P (powder):L (liquid) = 2.0/1.0 (P: 040344, L: 040314) | | |
| Ref. Ex. 2 | Fuji Luting S | | | 0209182 (Volume Ratio 1.4/1.0) | | |
| Ref. Ex. 3 | Panavia F 2.0 | | | Paste (A Paste: 0054AA, B Paste: 0009AA) Equivalent Volume Ratio ED Primer II (A Liquid: 00120B, B Liquid: 00026B) | | |

Reference Example 1

Currently commercially available HY-bond glass ionomer cement CX manufactured by Shofu Inc. was mixed at a ratio of a mixing weight ratio of 2.0 (powder): 1.0 (liquid). Although mixing was performed at once, a powder flied and, mixing was impossible and, therefore, a mixing procedure was preformed by the conventional divided mixing.

Reference Example 2

Two pastes from currently commercial available Fuji Luting S Cement (LOT.0209182) manufactured by GC CORPORATION were taken (mixing volumetric ratio of 1.4/1.0) through an annexed dispenser.

Reference Example 3

Currently commercially available Panavia F2.0 (A paste: LOT.0054AA, B paste: LOT.0009AA) manufactured by Kuraray Medical was mixed at a ratio of a mixing volumetric ratio equivalent.

Example 13

Test of Assessing Performance of Cement Composition

Respective cement compositions prepared in Examples 1 to 12, Comparative Examples 1 to 6; and Reference Examples 1 to 3 were tested for handling, surface property conformation, water sensitivity, bending strength and adhesion to tooth substance. Details of each test are explained below.

(1) Handling Test

Test Purpose:

Handling feeling, mixing time and properties of a mixed material at mixing a paste/paste or a powder/liquid constituting a cement composition are evaluated.

Test Method:

A predetermined amount of a paste/paste or a powder/liquid are taken on a paper mixing plate, this is mixed, and handling feeling in mixing, a time necessary for production of a visually uniform mixed material (mixing time) and properties (viscosity, dropping, stringiness) of a mixed material are evaluated.

(2) Surface Property Confirmation Test

Test Purpose:

The presence or the absence of an unpolymerized layer on a surface of a cured cement composition are evaluated.

Test Method:

A predetermined amount of a paste/paste or a powder/liquid are taken on a paper mixing plate, and this is mixed until a uniform mixed material (cement composition) is produced. After completion of mixing, a mixed material (cement composition) is filled into a stainless mold (diameter 10×height 5 mm) placed on a glass plate.

Thereafter, an upper surface thereof is flattened using a spatula. Fifteen minutes after completion of mixing, the presence or the absence of an unpolymerized layer on a surface of a cured cement composition is confirmed by observation with naked eyes (luster feeling based on resin composition) and touch feeling (sticky feeling based on resin component).

In the case of a cement composition containing a photopolymerization catalyst, a mixed material is filled into a stainless mold, an upper surface thereof is flattened using a spatula and, immediately thereafter, light is irradiated using a visible light photopolymerization irradiator (Grip Light II: manufactured by Shofu Inc.) having an effective wavelength region of 400 to 500 nm, and the presence or the absence of an unpolymerized layer on a surface of a cured cement composition are confirmed similarly.

Evaluation Criteria:

Evaluation is performed according to the following evaluation criteria.

Presence of unpolymerized layer: the case where luster feeling based on a resin component is recognized visually or sticky feeling based on a resin component is recognized by touch feeling, on a surface of a cured cement composition.

Absence of unpolymerized layer: the case where neither luster feeling nor sticky feeling based on a resin composition is recognized.

(3) Water Sensitivity Test

Test Purpose:

Water sensitivity during a curing process in a cement composition is evaluated.

Test Method:

A predetermined amount of a paste/paste or a powder/liquid are taken on a paper mixing plate, and this is mixed until a uniform mixed material (cement composition) is produced. After completion of mixing, a cement composition is trimmed into one spherical mass on a paper mixing plate.

One minute after completion of mixing, a massy cement composition is immersed in water in a sample bottle retained at 37° C., and this is allowed to stand at 37° C. A curing reaction initiates from immediately after initiation of mixing, a curing rate depends on a cement composition and, one minute after completion of mixing, curing of any cement composition has not been completed yet. That is, by immersing in water during curing, influence of water on a curing reaction is confirmed.

In the case of a cement composition containing a photopolymerization catalyst, immediately after trimming a mixed material into a spherical mass, light is irradiated using a photopolymerization irradiator (Grip Light II: manufactured by Shofu Inc.) for 20 seconds, a cement composition which has been cured into a mass is immersed in water similarly, and this is allowed to stand at 37° C.

In any cement composition, fifteen minutes after immersion, a sample bottle is slightly shaken. Thereupon, the state of a massy cured cement composition and water is observed visually.

Evaluation Criteria:

Evaluation is performed according to the following evaluation criteria.

Presence of water sensitivity: the case where clear disintegration of a cured cement composition, or remarkable water clouding is recognized.

Absence of water sensitivity: the case where neither disintegration of a cured cement composition nor remarkable clouding of water is recognized.

(4) Bending Strength Test

Test Purpose:

A bending strength of a cured cement composition is evaluated.

Test Method:

(In the Case of a Cement Composition not Containing a Photopolymerization Catalyst)

A predetermined amount of a paste/paste or a powder/liquid are taken on a paper mixing plate, and this is mixed until a uniform mixed material (cement composition) is produced. After completion of mixing, a mixed material (cement composition) is filled in a dedicated mold (25×2×2 mm: rectangular parallelepiped type) for a bending strength test, and this is pressed with a pressurizer. One minute after completion of mixing, the material is allowed to stand in the atmosphere of a temperature of 37° C. and a humidity of 100% for 1 hour in the pressed state, to cure a mixed material (cement composition).

(In the Case of a Cement Composition Containing a Photopolymerization Catalyst)

A predetermined amount of a paste/paste or a powder/liquid are taken on a paper mixing plate, and this is mixed until a uniform mixed material (cement composition) is produced. After completion of mixing, a mixed material (cement composition) is filled into a dedicated mold (25×2×2 mm: rectangular parallelepiped type) for a bending strength test, a cover glass is placed thereon from an upper side, and this is pressed using a glass plate. One minute after completion of mixing, five places are irradiated with light for 30 seconds using a photopolymerization irradiator (Grip Light II: manufactured by Shofu Inc.) from over a cover glass, and this is allowed to stand in the atmosphere of a temperature of 37° C. and a humidity of 100% in that state, to cure a mixed material (cement composition).

(Common)

After allowing to stand for 1 hour, a cured material is taken out from a mold, and this is used as a test sample. The test sample is immersed in distilled water at 37° C. for 24 hours, and a bending strength is measured using Instron Universal testing machine (Instron 5567, manufactured by Instron) under the condition of a distance between the supports of 20 mm, and a crosshead speed of 1 mm/min. Ten test samples are measured, and the strength is evaluated as its average.

(5) Adhesion to Tooth Substance

Test Purpose:

Adhesion to tooth substance of a cement composition is evaluated.

Test Method;

A bovine mandibular permanent central incisor which was extracted after slaughter and freeze-stored within 24 hours is thawed, and a root is removed and a crown is cut to prepare a bovine tooth piece. The bovine tooth piece is embedded in an epoxy resin. An enamel or a dentin of the embedded bovine tooth is exposed with a No. 600 water resistant sandpaper under water pouring, and this is washed with water and dried to prepare a bovine tooth test piece.

A predetermined amount of a paste/paste or a powder/liquid are taken on a paper mixing plate, and this is mixed until a uniform mixed material (cement composition) is produced. The mixed material (cement composition) is coated on an adhering surface of a stainless bar, this is pushed against an enamel or a dentin on a surface of a bovine tooth test piece, and pressed under a constant load, and an extra material is removed to prepare an adhesion test piece.

In a cement composition containing a photopolymerization catalyst, a stainless bar is pressed under a constant load, two places on a diagonal line are irradiated with light for 10 seconds from a side direction of an adhered part using a photopolymerization irradiator (Grip Light II: manufactured by Shofu Inc.), and an extra material is removed to prepare an adhesion test piece.

The adhesion test piece is allowed to stand to cure in the atmosphere of a temperature of 37° C. and a humidity of 100% for 1 hour in the pressed state. After one hour, the adhesion test piece is immersed in distilled water at 37° C. for 24 hours, and a tensile adhesion strength is measured at a crosshead speed of 1 mm/min using an Instron Universal testing machine (Instron 5567, manufactured by Instron) Six test samples are measured, and are evaluated by its average.

Results of a handling test, a surface property confirmation test, water sensitivity test, a bending strength test and an adhesion to tooth substance test which were performed using cement compositions 1 to 12 obtained in Examples 1 to 12 are shown in Table 5.

Since a cement composition 12 obtained in Example 12 contains also a photopolymerization catalyst, regarding this cement composition, a surface property confirmation test, a water sensitivity test, a bending strength test and an adhesion to tooth substance test were performed according to each test method for a composition containing a photopolymerization catalyst and a composition not containing a photopolymerization catalyst.

TABLE 5

Test Results for Two Paste Type Glass Ionomer Cement of the Present Invention

| | | Handling | | | Property of Surface | | Bending | Adhesion to Tooth Substance | | |
|---|---|---|---|---|---|---|---|---|---|---|
| | Cement Component | Feeling in Mixing | Mixing Time (s) | Property of Mixture | Unpolymerized Layer | Water Sensitivity | Strength (MPa) | Enamel (MPa) | Dentin (MPa) | Remarks |
| Ex. 1 | 1 | ○ | 10 | GOOD | NO | NO | 38 | 4.2 | 2.7 | |
| Ex. 2 | 2 | ○ | 10 | GOOD | NO | NO | 33 | 2.8 | 1.7 | |
| Ex. 3 | 3 | ○ | 10 | GOOD | NO | NO | 40 | 5.3 | 1.5 | |
| Ex. 4 | 4 | ○ | 10 | GOOD | NO | NO | 44 | 6.3 | 2.4 | |
| Ex. 5 | 5 | ○ | 10 | GOOD | NO | NO | 43 | 5.5 | 2.0 | |
| Ex. 6 | 6 | ○ | 10 | GOOD | NO | NO | 37 | 2.9 | 2.4 | |
| Ex. 7 | 7 | ○ | 10 | GOOD | NO | NO | 35 | 2.6 | 1.8 | |
| Ex. 8 | 8 | ○ | 5 | GOOD | NO | NO | 23 | 2.5 | 1.4 | |
| Ex. 9 | 9 | ○ | 10 | GOOD | NO | NO | 37 | 4.8 | 2.0 | |
| Ex. 10 | 10 | ○ | 10 | GOOD | NO | NO | 39 | 4.8 | 1.7 | |
| Ex. 11 | 11 | ○ | 10 | GOOD | NO | NO | 36 | 3.0 | 2.0 | |
| Ex. 12 | 12 | ○ | 10 | GOOD | NO | NO | 33 | 2.9 | 1.8 | No Light Irradiation |
| | | | | | NO | NO | 37 | 3.7 | 2.4 | Light Irradiation |

Results of a handling test, a surface property confirmation test, a water sensitivity test, a bending strength test and an adhesion to tooth substance test which were performed using cement compositions 13 to 18 obtained in Comparative Examples 1 to 6 are shown in Table 6.

Results of a handling test, a surface property confirmation test, a water sensitivity test, a bending strength test and adhesion to tooth substance test which were performed using cement compositions obtained in Reference Examples 1 to 3 are shown in Table 6.

An adhesion to tooth substance test regarding a cement composition obtained in Reference Example 3 was performed according to a test method of a cement composition containing a photopolymerization catalyst after an annexed ED primer II (A liquid: LOT.00120B, B liquid: LOT.00026B) was pre-treated according to instructions of a manufacturer.

As shown in Table 5, in the cement composition 12 obtained in Example 12, the same tendency as that of cement compositions 1 to 11 was recognized in every test regardless of the presence or the absence of light irradiation (the presence or the absence of a curing mechanism due to photopolymerization), and the effect of light irradiation was hardly recognized in each test.

However, when light is not irradiated, one has to wait until curing of a cement composition is completed, but when light is irradiated, it is not necessary to wait until curing of a cement composition is completed, thereby, curing can be instantaneously completed by light irradiation during a curing process. Therefore, it was recognized that a cement composition 12 containing a photopolymerization catalyst is useful for use in a site where a cavity is filled after caries treatment, or a sealant is irradiated with light.

TABLE 6

Test Results for Two Paste Type Glass Ionomer Cement in Comparative Examples and Reference Examples

|  | Cement Component | Handling | | Property of Surface | | Adhesion to | | | |
|  |  | Feeling in Mixing | Mixing Time (s) | Property of Mixture | Unpolymerized Layer | Water Sensitivity | Bending Strength (MPa) | Tooth Substance | | |
|  |  |  |  |  |  |  |  | Enamel (MPa) | Dentin (MPa) | Remarks |
|---|---|---|---|---|---|---|---|---|---|---|
| Com. Ex. 1 | 13 | ○ | 10 | GOOD | YES | NO | 10 | 0.4 | ND | |
| Com. Ex. 2 | 14 | ○ | 10 | GOOD | YES | YES | 22 | 1.7 | 0.2 | |
| Com. Ex. 3 | 15 | x | 15 | BAD | YES | NO | 31 | 0.6 | ND | |
| Com. Ex. 4 | 16 | ○ | 10 | GOOD | YES | YES | 28 | 4.4 | 1.8 | |
| Com. Ex. 5 | 17 | x | 15 | GOOD | YES | YES | 5 | 7.3 | 2.3 | |
| Com. Ex. 6 | 18 | x | 15 | GOOD | YES | YES | 12 | 6.5 | 1.8 | |
| Ref. Ex. 1 | HY-Bond Glass Ionomer Cement CX | x | 30 | BAD | NO | YES | 20 | 2.3 | 1.5 | |
| Ref. Ex. 2 | Fuji Luting S | ○ | 10 | GOOD | YES | NO | 25 | 2.1 | 0.4 | |
| Ref. Ex. 3 | Panavia F2.0 | ○ | 10 | GOOD | YES | NO | 115 | 20.0 | 7.0 | |

ND (No Data): Measurement was impossible due to peeling-off.

As shown in Table 5, it was recognized that cement compositions 1 to 11 obtained in Examples 1 to 11 are excellent in handling, a bending strength, water sensitivity, and dental adhesion to a dentin or an enamel, as compared with the conventional glass ionomer cements (Reference Examples 1 to 3).

Particularly, regarding handling, divisional mixing which has been performed at mixing a resin-modified glass ionomer cement which is a powder-liquid type, or the conventional glass ionomer cement is not necessary, at once-mixing is possible, and a powder does not fly due to a paste type, and a procedure of mixing is not necessary and, therefore, feeling in mixing is extremely better.

In addition, a time necessary for production of a uniform mixed material (cement composition) is very short as within 10 seconds as compared with the conventional glass ionomer cement, a property of a mixed material (cement composition) is not accompanied with sticking, dropping and stringiness, and the mixed material has such a creamy state that operation after mixing is easy and, therefore, better handling was recognized.

The presence of an unpolymerized layer which has been observed in the conventional resin-modified glass ionomer cement (power-liquid type•pate-paste type) and resin cements (Comparative Examples 1 to 6) was not recognized on a surface of a cured material of these cement compositions, and it was recognized that the cured material has surface curability equivalent to that of the conventional glass ionomer cement.

As shown in Table 6, since a cement composition 13 obtained in Comparative Example 1 does not contain (b) a polymer of acidic group-containing polymerizable monomers which is a constitutional component for an acid-base reaction, the composition has little dental adhesion to a dentin or an enamel, and it was recognized that a bending strength is low.

In addition, the presence of an unpolymerized layer was recognized on a surface of a cured cement composition 13 as in a resin cement.

As shown in Table 6, since a cement composition 14 obtained in Comparative Example 2 does not contain (e) an acid reactive filler which is a constitutional component for an acid-base reaction, it was recognized that dental adhesion to a dentin or an enamel is low, and a bending strength is also low.

In addition, on a surface of a cured cement composition 14, the presence of an unpolymerized layer was recognized as in a resin cement and, further; water sensitivity which is shortcoming of the conventional glass ionomer cement was recognized.

As shown in Table 6, since a cement composition 15 obtained in Comparative Example 3 does not contain (d) water which is a constitutional component for an acid-base reaction, handling was recognized to be worse.

In addition, low dental adhesion to a dentin or an enamel was recognized.

Further, on a surface of a cured cement composition 15, the presence of an unpolymerized layer was recognized as in a resin cement.

As shown in Table 6, since a cement composition 16 obtained in Comparative Example 4 does not contain (f) a polymerization catalyst which is a constitutional component for a polymerization reaction, (a) a hydrophobic polymerizable monomer and (c) a hydrophilic polymerizable monomer can not be polymerized.

For this reason, the presence of an unpolymerized layer was recognized on a surface of a cured cement composition 16 as in a resin cement and, further, since the presence of the resin component inhibits an acid-base reaction to delay curing, the cured material has water sensitivity.

As shown in Table 6, although in a cement composition 17 obtained in Comparative Example 5, two pastes at initial mixing have worse miscibility and, therefore, a little time is required until a uniform mixed material is produced, there is particularly no problem of a property of a mixed material, and the composition has such a property that the material is easily operated.

However, on a surface of a cured cement composition 17, the presence of an unpolymerized layer was recognized as in a resin cement and, further, water sensitivity which is shortcoming of the conventional glass ionomer cement was recognized.

As shown in Table 6, the same result as that of a cement composition 17 was recognized in a cement composition 18 obtained in Comparative Example 6.

As shown in Table 6, in HY-Bond glass ionomer cement CX, feeling in mixing was worse because mixture state of a powder and a liquid during mixing procedure is incompleteness, and a long mixing time (30 seconds) was required for producing a uniform mixed material (cement composition). Further, in a property of a mixed material (cement composition), it was recognized that since sticking or dropping is accompanied, handling is worse.

Surface curability of this mixed material is better, but water sensitivity was recognized.

Further, it was recognized that a bending strength and adhesion to tooth substance are low.

As shown in Table 6, Fuji Luting S had better handling, and water sensitivity was not recognized, but the presence of an unpolymerized layer was recognized on a surface of a cured mixed material.

In addition, a bending strength and adhesion to tooth substance were low being almost the same as those of the conventional glass ionomer cement.

As shown in Table 6, in Panavia F2.0, handling was better, and water sensitivity was not recognized, but the presence of an unpolymerized layer was recognized on a surface of a cured mixed material.

In addition, a bending strength and adhesion to tooth substance exhibit high values. However, for obtaining high adhesion to tooth substance, it is necessary to use dedicated ED primer II.

What is claimed is:

1. A two paste glass ionomer cement which comprises a resin-based paste and a water-based paste, which is characterized in that:

the resin-based paste is substantially free of water and comprises (a) a hydrophobic polymerizable monomer and (b) a polymer of acidic group-containing polymerizable monomers, wherein (a) the hydrophobic polymerizable monomer and (b) the polymer of acidic group-containing polymerizable monomers are insoluble to each other and (b) the polymer of acidic group-containing polymerizable monomers exists in a solid state in the resin-based paste, and the water-based paste comprises (c) a hydrophilic polymerizable monomer and (d) water, wherein (c) the hydrophilic polymerizable monomer and (d) the water are soluble to each other, and wherein (1) at least one of the resin-based paste and the water-based paste contains (e) an acid reactive filler and (f) a polymerization catalyst together;

(2) the resin-based paste contains (e) an acid reactive filler and the water-based paste contains (f) a polymerization catalyst; or (3) the resin-based paste contains (f) a polymerization catalyst and the water-based paste contains (e) an acid reactive filler.

2. The two paste glass ionomer cement according to claim 1, wherein a total amount of (e) the acid reactive filler, (b) the polymer of acidic group-containing polymerizable monomers and (d) the water is in a range of 40 to 90 parts by weight per 100 parts by weight of the glass ionomer cement, and (e) the acid reactive filler:(b) the polymer of acidic group-containing polymerizable monomers:(d) the water is in a range of 1:0.1-2.9:0.1-3.6.

3. The two paste glass ionomer cement according to claim 1, wherein the resin-based paste contains (g) an acidic group-containing polymerizable monomer.

4. The two paste glass ionomer cement according to claim 1, wherein (b) the polymer of acidic group-containing polymerizable monomers is a polymer of an α-β unsaturated carboxylic acidic group-containing polymerizable monomer.

5. The two paste glass ionomer cement according to claim 1, wherein (e) the acid reactive filler is a fluorine-containing radiopaque acid reactive glass filler which comprises fluorine and an element having radiopacity.

6. The two paste glass ionomer cement according to claim 1, wherein (f) the polymerizing catalyst is a barbituric acid derivative selected from the group consisting of barbituric acid, 1,3-dimethylbarbituric acid, 1,3-diphenylbarbituric acid, 1,5-dimethylbarbituric acid, 5-butylbarbituric acid 5-ethylbarbituric acid, 5-isopropylbarbituric acid 5-cyclohexylbarbituric acid 1,3,5-trimethylbarbituric acid, 1,3-dimethyl-5-ethylbarbituric acid 1,3-dimethyl-n-butylbarbituric acid, 1,3-dimethyl-5-isobutylbarbituric acid, 1,3-dimethylbarbituric acid 1,3-5-cyclopentylbarbituric acid 1,3-dimethyl-5-cyclohexylbarbituric acid, 1,3-dimethyl-5-phenylbarbituric acid, 1-cyclohexyl-5-ethylbarbituric acid, 1-benzyl-5-phenlbarbituric acid and thiobarbituric acids, alkali metal salts thereof and alkaline earth metal salts thereof, or an organic peroxide-tertiary amine redox catalyst or a combination thereof.

* * * * *

UNITED STATES PATENT AND TRADEMARK OFFICE
CERTIFICATE OF CORRECTION

PATENT NO. : 7,488,762 B2  Page 1 of 1
APPLICATION NO. : 11/409268
DATED : February 10, 2009
INVENTOR(S) : Satosi Takano It is certified that error appears in the above-identified patent and that said Letters Patent is hereby corrected as shown below:

Title Pg, Item (75) Inventors:
The residence of the fourth Inventor, Shinji Urabe, should be "Hyogo" (not "Kyoto").

Title Pg, Item (75) Inventors:
The residence of the fifth Inventor, Toshimasa Ohnishi, should be "Hyogo" (not "Kyoto").

Title Pg, Item (73) Assignees:
The residence of the Assignee, Kabushiki Kaisha Shofu, should be "Kyoto" (not "Osaka").

Signed and Sealed this

Twelfth Day of May, 2009

JOHN DOLL
*Acting Director of the United States Patent and Trademark Office*